(12) United States Patent
Kelson et al.

(10) Patent No.: US 12,076,583 B2
(45) Date of Patent: Sep. 3, 2024

(54) DIFFUSING ALPHA-EMITTER RADIATION THERAPY FOR MELANOMA

(71) Applicant: ALPHA TAU MEDICAL LTD., Jerusalem (IL)

(72) Inventors: Itzhak Kelson, Tel Aviv (IL); Yona Keisari, Ramat Gan (IL); Amnon Gat, Matan (IL); Robert Den, Merion Station, PA (US); Ofer Magen, Hod Hasharon (IL); Vered Domankevich, Hod Hasharon (IL); Lior Arazi, Tel Aviv (IL); Tomer Cooks, Gedera (IL); Guy Heger, Ramat Gan (IL); Mirta Dumančić, Beer Sheva (IL); Ishai Luz, Kibbutz Gevim (IL); Maayan Hedva Vatarescu, Lehavim (IL)

(73) Assignee: ALPHA TAU MEDICAL LTD., Jerusalem (IL)

( * ) Notice: Subject to any disclaimer, the term of this patent is extended or adjusted under 35 U.S.C. 154(b) by 0 days.

(21) Appl. No.: 18/094,424

(22) Filed: Jan. 9, 2023

(65) Prior Publication Data
US 2023/0143006 A1 May 11, 2023

Related U.S. Application Data

(63) Continuation of application No. PCT/IB2022/055328, filed on Jun. 8, 2022, which is
(Continued)

(51) Int. Cl.
*A61N 5/10* (2006.01)

(52) U.S. Cl.
CPC ......... *A61N 5/1027* (2013.01); *A61N 5/1007* (2013.01); *A61N 5/103* (2013.01); *A61N 2005/1024* (2013.01)

(58) Field of Classification Search
CPC .................................................. A61N 5/1027
See application file for complete search history.

(56) References Cited

U.S. PATENT DOCUMENTS

| 5,205,289 A | 4/1993 | Hardy et al. |
| 6,099,458 A | 8/2000 | Robertson |

(Continued)

FOREIGN PATENT DOCUMENTS

| EP | 1815873 A1 | 8/2007 |
| RU | 2606108 C2 | 1/2017 |

(Continued)

OTHER PUBLICATIONS

Popovtzer et al., "Initial Safety and Tumor Control Results from a "First-in-Human" Multicenter Prospective Trial Evaluating a Novel Alpha-Emitting Radionuclide for the Tretament of Locally Advanced Recurrent Squamos Cell Carcinomas of the Skin and Head and Neck," International Journal of Radiation Oncology—Biology—Physics, vol. 106, issue 3, pp. 571-578, Mar. 1, 2020.

(Continued)

*Primary Examiner* — Thaddeus B Cox
(74) *Attorney, Agent, or Firm* — MEITAR PATENTS LTD.

(57) ABSTRACT

A method for treating a tumor, comprising identifying a tumor as a melanoma tumor and implanting in the tumor identified as a melanoma tumor, at least one diffusing alpha-emitter radiation therapy (DaRT) source (21) with a suitable radon release rate and for a given duration, such that the source (21) provides during the given duration a cumulated activity of released radon between 3.2 Mega becquerel (MBq) hour and 7.5 MBq hour, per centimeter length.

7 Claims, 14 Drawing Sheets

Related U.S. Application Data a continuation-in-part of application No. 17/343,789, filed on Jun. 10, 2021, now abandoned.

(56) References Cited

U.S. PATENT DOCUMENTS

| | | | |
|---|---|---|---|
| 6,248,057 | B1 | 6/2001 | Mavity et al. |
| 6,635,234 | B1 | 10/2003 | Larsen et al. |
| 6,638,205 | B1 | 10/2003 | Chan et al. |
| 8,821,364 | B2 | 9/2014 | Fisher et al. |
| 8,834,837 | B2 | 9/2014 | Kelson et al. |
| 8,894,969 | B2 | 11/2014 | Kelson et al. |
| 10,166,403 | B2 | 1/2019 | Bakker et al. |
| 2001/0005930 | A1 | 7/2001 | Coniglione |
| 2003/0018232 | A1 | 1/2003 | Elliott et al. |
| 2005/0080314 | A1 | 4/2005 | Terwilliger et al. |
| 2009/0234175 | A1 | 9/2009 | Maier |
| 2010/0015042 | A1 | 1/2010 | Keisari et al. |
| 2010/0178245 | A1 | 7/2010 | Arnsdorf et al. |
| 2010/0200778 | A1 | 8/2010 | Drobnik et al. |
| 2011/0184283 | A1 | 7/2011 | Rivard |
| 2013/0225901 | A1 | 8/2013 | Krishnan et al. |
| 2016/0250360 | A1 | 1/2016 | Larsen |
| 2017/0058360 | A1 | 3/2017 | Theodorescu et al. |
| 2019/0099620 | A1 | 4/2019 | Isola et al. |
| 2020/0114004 | A1 | 4/2020 | Tuli |
| 2021/0008233 | A1 | 1/2021 | Kelson et al. |
| 2022/0184418 | A1 | 6/2022 | Arazi et al. |
| 2022/0212035 | A1 | 7/2022 | Kelson et al. |
| 2022/0395700 | A1 | 12/2022 | Kelson et al. |
| 2022/0395701 | A1 | 12/2022 | Kelson et al. |
| 2022/0395702 | A1 | 12/2022 | Kelson et al. |
| 2022/0395703 | A1 | 12/2022 | Kelson et al. |
| 2022/0395704 | A1 | 12/2022 | Kelson et al. |
| 2022/0395706 | A1 | 12/2022 | Kelson et al. |
| 2022/0401755 | A1 | 12/2022 | Kelson et al. |

FOREIGN PATENT DOCUMENTS

| | | | |
|---|---|---|---|
| WO | 9719706 | A1 | 6/1997 |
| WO | 9917812 | A1 | 4/1999 |
| WO | 2006003123 | A2 | 1/2006 |
| WO | 2006110889 | A2 | 10/2006 |
| WO | 2007013060 | A1 | 2/2007 |
| WO | 2018207105 | A1 | 11/2018 |
| WO | 2019171308 | A1 | 9/2019 |
| WO | 2019193464 | A1 | 10/2019 |
| WO | 2020089819 | A1 | 5/2020 |
| WO | 2022148985 | A1 | 7/2022 |

OTHER PUBLICATIONS

Arazi, "Diffusing Alpha-Emitters Radiation Therapy: Approximate Modeling of the Macroscopic Alpha Particle Dose of a Point Source," Physics in Medicine & Biology, vol. 65, issue 1, pp. 1-24, year 2020.
Feliciani et al., "Diffusing Alpha-Emitters Radiation Therapy (DaRT): Template Based Treatment Planning Technique for Brachytherapy of Squamous Cell Skin Cancer," Abstracts/Physica Medica, vol. 52, p. 35, year 2018.
Arazi et al., "Diffusing Alpha Emitters Radiation Therapy: Theoretical Modeling," International Journal of Radiation Oncology—Biology—Physics, Pergamon Press, vol. 108, No. 3, p. e336, Oct. 23, 2020.
Arazi et al., "Alpha DaRT: Revoluionary Alpha-Emitters Brachytherapy," Journal of Medical Imaging and Radiation Sciences, Elsevier, Amsterdam, NL, vol. 50, No. 4, p. S96, Dec. 1, 2019.
European Application # 22178053.9 Search report dated Nov. 3, 2022.
International Application # PCT/IB2022/055322 Search Report dated Nov. 15, 2022.
EP Application # 22178051.3 Search Report dated Nov. 2, 2022.
International Application # PCT/IB2022/055325 Search Report dated Nov. 17, 2022.
International Application # PCT/IB2022/055324 Search Report dated Nov. 17, 2022.
EP Application # 22178060.4 Search Report dated Nov. 3, 2022.
International Application # PCT/IB2022/055323 Search Report dated Nov. 15, 2022.
International Application # PCT/IB2022/055326 Search Report dated Nov. 17, 2022.
International Application # PCT/IB2022/055327 Search Report dated Nov. 20, 2022.
International Application # PCT/IB2022/055328 Search Report dated Nov. 20, 2022.
International Application # PCT/IB2022/055329 Search Report dated Nov. 21, 2022.
GE Healthcare, "Typhoon FLA 9000 Biomolecular Imager," Data File 28-9610-72 AB, General Electric Company, pp. 1-8, years 2009-2010.
The University of Arizona: "Startup with an Innovative Imaging System Wins Sponsored Launch," News, Tech Parks Arizona, pp. 1-4, year 2020.
"Imaging Plates", Product Description, pp. 1-15, Jun. 12, 2007 Downloaded from https://www.buero-analytik-winden.de/app/download/13602912/Imaging+plates+ausf%C3% BChrliche+Beschreibung.pdf.
Kelson et al., U.S. Appl. No. 18/094,429, filed Jan. 9, 2023.
Kelson et al., U.S. Appl. No. 18/094,406, filed Jan. 9, 2023.
Kelson et al., U.S. Appl. No. 18/094,408, filed Jan. 9, 2023.
Kelson et al., U.S. Appl. No. 18/094,411, filed Jan. 9, 2023.
Kelson et al., U.S. Appl. No. 18/094,416, filed Jan. 9, 2023.
Kelson et al., U.S. Appl. No. 18/094,419, filed Jan. 9, 2023.
Kelson et al., U.S. Appl. No. 18/094,421, filed Jan. 9, 2023.
Arazi et al., "The Treatment of Solid Tumors by Alpha Emitters Released from (224)Ra-loaded Sources—Internal Dosimetry Analysis," Physics in Medicine and Biology, vol. 55, pp. 1203-1218, year 2010.
Arazi, "Diffusing Alpha-Emitters Radiation Therapy: Theoretical and Experimental Dosimetry," PH.D. Thesis, Raymond and Beverly Sackler Faculty of Exact Sciences, School of Physics and Astronomy, Tel Aviv University, pp. 1-285, Sep. 2008.
U.S. Appl. No. 18/094,416 Office Action dated Apr. 12, 2023.
U.S. Appl. No. 18/094,406 Office Action dated Apr. 24, 2023.
U.S. Appl. No. 18/094,421 Office Action dated May 9, 2023.
U.S. Appl. No. 18/094,411 Office Action dated May 9, 2023.
AU Application # 2022204082 Office Action dated May 22, 2023.
AU Application # 2022204083 Office Action dated May 22, 2023.
AU Application # 2022204084 Office Action dated May 22, 2023.
U.S. Appl. No. 18/094,429 Office Action dated Jun. 14, 2023.
U.S. Appl. No. 18/094,419 Office Action dated Jun. 16, 2023.
U.S. Appl. No. 18/094,408 Office Action dated Jun. 16, 2023.
U.S. Appl. No. 17/549,929 Office Action dated Aug. 24, 2023.
U.S. Appl. No. 18/094,429 Office Action dated Sep. 29, 2023.
U.S. Appl. No. 18/094,406 Office Action dated Aug. 21, 2023.
U.S. Appl. No. 18/094,408 Office Action dated Oct. 10, 2023.
U.S. Appl. No. 18/094,411 Office Action dated Aug. 21, 2023.
U.S. Appl. No. 18/094,416 Office Action dated Sep. 29, 2023.
U.S. Appl. No. 18/094,419 Office Action dated Oct. 10, 2023.
U.S. Appl. No. 18/094,421 Office Action dated Aug. 22, 2023.
U.S. Appl. No. 18/094,411 Office Action dated Dec. 18, 2023.
U.S. Appl. No. 18/094,406 Office Action dated Dec. 15, 2023.
AU Application # 2022204082 Office Action dated Dec. 20, 2023.
U.S. Appl. No. 18/094,419 Office Action dated Jan. 29, 2024.
U.S. Appl. No. 18/094,408 Office Action dated Jan. 29, 2024.
U.S. Appl. No. 18/094,421 Office Action dated Dec. 19, 2023.
U.S. Appl. No. 18/094,416 Office Action dated Feb. 29, 2024.

DIFFUSING ALPHA-EMITTER RADIATION THERAPY FOR MELANOMA

CROSS-REFERENCE TO RELATED APPLICATIONS

This application is a continuation of PCT application PCT/IB2022/055328, filed Jun. 8, 2022, which is a continuation-in-part of U.S. patent application Ser. No. 17/343,789, filed Jun. 10, 2021, now abandoned. The disclosures of these related applications are incorporated herein by reference.

FIELD OF THE INVENTION

The present invention relates generally to radiotherapy and particularly to apparatus and methods for providing tumor-specific radiation dosages in radiotherapy treatment.

BACKGROUND OF THE INVENTION

Ionizing radiation is commonly used in the treatment of certain types of tumors, including malignant cancerous tumors, to destroy their cells. Ionizing radiation, however, can also damage healthy cells of a patient, and therefore care is taken to minimize the radiation dose delivered to healthy tissue outside of the tumor, while maximizing the dose to the tumor.

Ionizing radiation destroys cells by creating damage to their DNA. The biological effectiveness of different types of radiation in killing cells is determined by the type and severity of the DNA lesions they create. Alpha particles are a powerful means for radiotherapy since they induce clustered double-strand breaks on the DNA, which cells cannot repair. Unlike conventional types of radiation, the destructive effect of alpha particles is also largely unaffected by low cellular oxygen levels, making them equally effective against hypoxic cells, whose presence in tumors is a leading cause of failure in conventional radiotherapy based on photons or electrons. In addition, the short range of alpha particles in tissue (less than 100 micrometers) ensures that if the atoms which emit them are confined to the tumor volume, surrounding healthy tissue will be spared. On the other hand, the short range of alpha radiation has so far limited their use in cancer therapy, as there was no practical way to deploy alpha emitting atoms in sufficient concentrations throughout the entire tumor volume.

Diffusing alpha-emitters radiation therapy (DaRT), described for example in U.S. Pat. No. 8,834,837 to Kelson, extends the therapeutic range of alpha radiation, by using radium-223 or radium-224 atoms, which generate chains of several radioactive decays with a governing half-life of 3.6 days for radium-224 and 11.4 days for radium-223. In DaRT, the radium atoms are attached to a source (also referred to as a "seed") implanted in the tumor with sufficient strength such that they do not leave the source in a manner that they go to waste (by being cleared away from the tumor through the blood), but a substantial percentage of their daughter radionuclides (radon-220 in the case of radium-224 and radon-219 in the case of radium-223) leave the source into the tumor, upon radium decay. These radionuclides, and their own radioactive daughter atoms, spread around the source by diffusion up to a radial distance of a few millimeters before they decay by alpha emission. Thus, the range of destruction in the tumor is increased relative to radionuclides which remain with their daughters on the source.

In order for the treatment of a tumor to be effective, DaRT seeds employed in the treatment should release a sufficient number of radon atoms to destroy the tumor with a high probability. If an insufficient amount of radiation is employed, too many cancerous cells will remain in the tumor, and these cells may reproduce to reform the malignant tumor. On the other hand, the seeds should not release too many radon atoms, as some of their daughters are cleared from the tumor through the blood and could therefore damage distant healthy tissue, including organs such as bone marrow, kidneys and/or ovaries of a patient.

The amount of radium atoms on the DaRT source is quantified in terms of the activity, i.e., the rate of radium decays. The DaRT source activity is measured in units of micro-Curie ($\mu$Ci) or kilo-Becquerel (kBq), where 1 $\mu$Ci=37 kBq=37,000 decays per second. When using DaRT, the radiation dose delivered to the tumor cells depends not only on the radium activity of the source, but also on the probability that the daughter radon atoms will leave the source into the tumor, upon radium's alpha decay. This probability is referred to herein as the "desorption probability". Thus, instead of referring to the activity of the source, one can use the "radon release rate", which is defined herein as the product of activity on the source and the desorption probability of radon from the source, as a measure of the DaRT related activity of a source. Like the activity, the radon release rate is given in $\mu$Ci or kBq. The activity and radon release rate values given herein are, unless stated otherwise, of the source at the time of implantation of the source in the tumor.

The above mentioned U.S. Pat. No. 8,834,837 to Kelson suggests using an activity "from about 10 nanoCurie to about 10 microCurie, more preferably from about 10 nanoCurie to about 1 microCurie."

SUMMARY OF THE INVENTION

Embodiments of the present invention relate to providing accurately tailored amounts of radiation to a tumor in a radiotherapy treatment. The embodiments include radiotherapy sources designed to provide suitable amounts of radiation, and kits including a suitable number of sources for tumors of specific sizes. Further embodiments relate to methods of preparing kits of radiotherapy sources for a specific tumor and methods of treatment of a tumor.

There is therefore provided in accordance with an embodiment of the present invention, a method for treating a melanoma tumor, comprising identifying a tumor as a melanoma tumor; and implanting in the tumor identified as a melanoma tumor, at least one diffusing alpha-emitter radiation therapy (DaRT) source with a suitable radon release rate and for a given duration, such that the source provides during the given duration a cumulated activity of released radon between 3.2 Mega becquerel (MBq) hour and 7.5 MBq hour, per centimeter length.

Optionally, implanting the at least one radiotherapy source comprises implanting an array of sources, each source separated from its neighboring sources in the array by not more than 4 millimeters. In some embodiments, implanting the at least one radiotherapy source comprises implanting an array of sources in a hexagonal arrangement, each source separated from its neighboring sources in the array by not more than 4 millimeters. Optionally, the at least one radiotherapy source has a radon release rate of between 0.67 and 1.6 microcurie per centimeter length. Optionally, the at least one radiotherapy source has a radon release rate of between 0.8 and 1.5 microcurie per centimeter length. Optionally, the method comprises selecting the given duration before implanting the at least one DaRT source in the tumor, and removing the sources from the tumor after the given duration from the implanting of the sources passed.

There is further provided in accordance with an embodiment of the present invention, a method of preparing a radiotherapy treatment, comprising identifying a tumor as a melanoma tumor, receiving an image of the melanoma tumor; and providing a layout of diffusing alpha-emitter radiation therapy (DaRT) sources for the melanoma tumor, wherein the sources have a radon release rate of between 0.67 and 1.6 microcurie per centimeter length. Optionally, providing the layout comprises providing a layout in which a spacing between sources in the tumor is 4 millimeters or less. Optionally, the sources have a radon release rate of between 0.8 and 1.5 microcurie per centimeter length.

There is further provided in accordance with an embodiment of the present invention, an apparatus for preparing a radiotherapy treatment, comprising an input interface for receiving information on a tumor, a processor configured to determine that the tumor is a melanoma tumor and to generate a layout of diffusing alpha-emitter radiation therapy (DaRT) sources for the tumor, wherein the sources in the layout have a radon release rate of between 0.67 and 1.6 microcurie per centimeter length and the sources in the layout are arranged in a regular pattern having a distance between adjacent sources of not more than 5 millimeters; and an output interface for displaying the layout to a human operator.

There is further provided in accordance with an embodiment of the present invention, a method of preparing a radiotherapy treatment, comprising receiving a request for diffusing alpha-emitter radiation therapy (DaRT) sources for a melanoma tumor, determining a number of radiotherapy sources required for the melanoma tumor, and providing a sterile kit including the determined number of radiotherapy sources, wherein the sources have a radon release rate of between 0.67 and 1.6 microcurie per centimeter length.

Optionally, determining the number of required radiotherapy sources comprises determining a number of sources required such that the area of the tumor is covered by sources with a spacing between the sources which is not greater than 4 millimeters. Optionally, the sources have a radon release rate of between 0.8 and 1.5 microcurie per centimeter length.

There is further provided in accordance with an embodiment of the present invention, a diffusing alpha-emitter radiation therapy (DaRT) source for implantation in a melanoma tumor, wherein the DaRT source has a radon release rate of between 0.67 and 1.6 microcurie per centimeter length. Optionally, the radon release rate is between 0.8 and 1.5 microcurie per centimeter length.

There is further provided in accordance with an embodiment of the present invention, a kit of diffusing alpha-emitter radiation therapy (DaRT) source for implantation in a melanoma tumor, comprising a sterile package; and a plurality of DaRT sources placed in the sterile package, the sources having a radon release rate of between 0.67 and 1.6 microcurie per centimeter length. Optionally, the radon release rate of the sources is between 0.8 and 1.5 microcurie per centimeter length.

There is further provided in accordance with an embodiment of the present invention, a method for treating a tumor, comprising identifying a tumor as a melanoma tumor, and implanting in the tumor identified as a melanoma tumor, an array of diffusing alpha-emitter radiation therapy (DaRT) sources, in a regular arrangement having a spacing between each two adjacent sources of between 3 and 4 millimeters. Optionally, implanting the array of sources comprises implanting in a hexagonal arrangement, each source separated from its neighboring sources in the array by not more than 3.5 millimeters.

DETAILED DESCRIPTION OF EMBODIMENTS

An aspect of some embodiments of the invention relates to setting radon release rates of DaRT sources used in treating different types of tumors according to characteristics of the tumors. Applicant has created a model which estimates the dose reaching the cells of a tumor, as a function of the diffusion length of lead-212 in the tumor, the diffusion length of radon-220 in the tumor and the leakage probability of lead-212. The diffusion length represents the typical distance from the point an atom was created in the decay of its parent radionuclide to the point where it decays. It determines the spatial distribution of the diffusing atoms around the seed; when the radial distance from the seed increases by one diffusion length, the alpha particle dose drops by approximately a factor of 3. For seeds with radon release rates considered here, the diameter of the region receiving an alpha particle dose of 10 Gy around the seed is roughly 10 times larger than the diffusion length. Methods of measuring an effective diffusion length and hence estimating the diffusion length of radon-220 and a range of values of the lead-212 diffusion length are described in the appendices. The leakage probability of lead-212 represents the chances that a lead-212 atom released from the source will leave a tumor through the blood system before it decays.

The diffusion lengths of radon-220 and the leakage probability of lead-212 have different values in different types of cancer tumors. Generally, the shorter the diffusion length of radon-220, the more activity is required to achieve similar results. Applicant has estimated the diffusion length of radon-220 in various types of tumors and accordingly has determined radon release rates of sources to be used in treating these tumor types.

Figure 1:
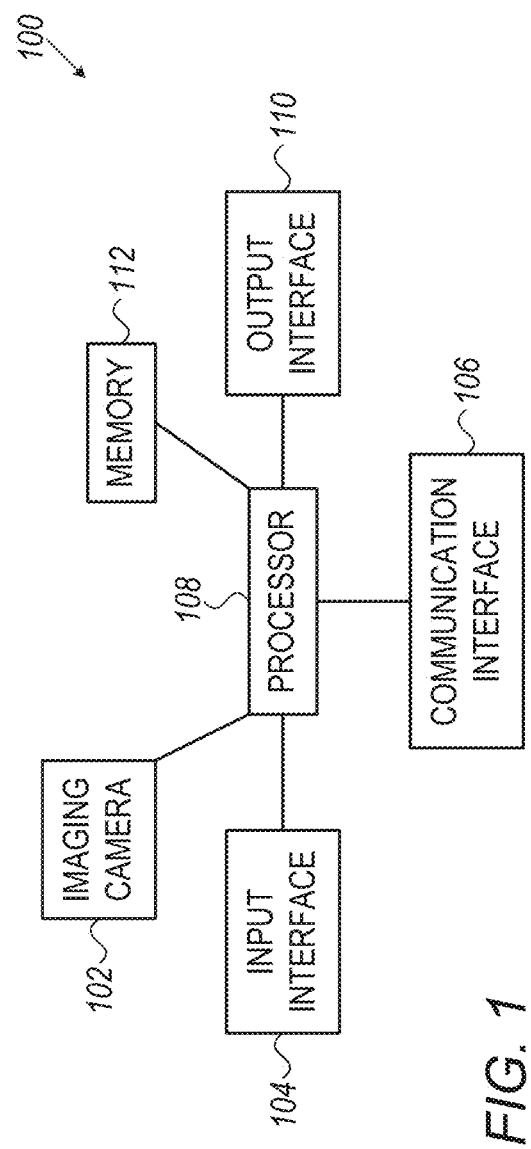
FIG. 1 is a schematic illustration of a system for planning a radiotherapy treatment, in accordance with an embodiment of the present invention.

FIG. 1 is a schematic illustration of a system 100 for planning a radiotherapy treatment, in accordance with an embodiment of the present invention. The treatment generally includes implantation of a plurality of sources in a tumor which is to be destroyed. System 100 comprises an imaging camera 102 which acquires images of tumors requiring radiotherapy. In addition, system 100 includes an input interface 104, such as a keyboard and/or mouse, for receiving input from a human operator, such as a physician. Alternatively or additionally, system 100 comprises a communication interface 106 for receiving instructions and/or data from a remote computer or human operator. System 100 further comprises a processor 108 configured to generate a layout plan of radiotherapy sources in the tumor and accordingly to provide through an output interface 110, details of respective kits of radiotherapy sources for treatment of the tumors. Output interface 110 may be connected to a display and/or to a communication network. Processor 108 optionally comprises a general purpose hardware processor configured to run software to execute its tasks described hereinbelow. Alternatively or additionally, processor 108 comprises a dedicated processor, such as a signal processing processor, a digital signal processor (DSP) or a vector processor, configured with suitable software for performing its tasks described herein. In other embodiments, processor 108 comprises a dedicated hardware processor configured in hardware, such as an FPGA or ASIC to perform its tasks.

In some embodiments, processor 108 is further configured to estimate the radiation dose expected to reach each of the points in the tumor, for example as described in PCT application PCT/IB2021/050034, filed Jan. 5, 2021, and titled "Treatment Planning for Alpha Particle Radiotherapy", the disclosure of which is incorporated herein by reference.

Figure 2:
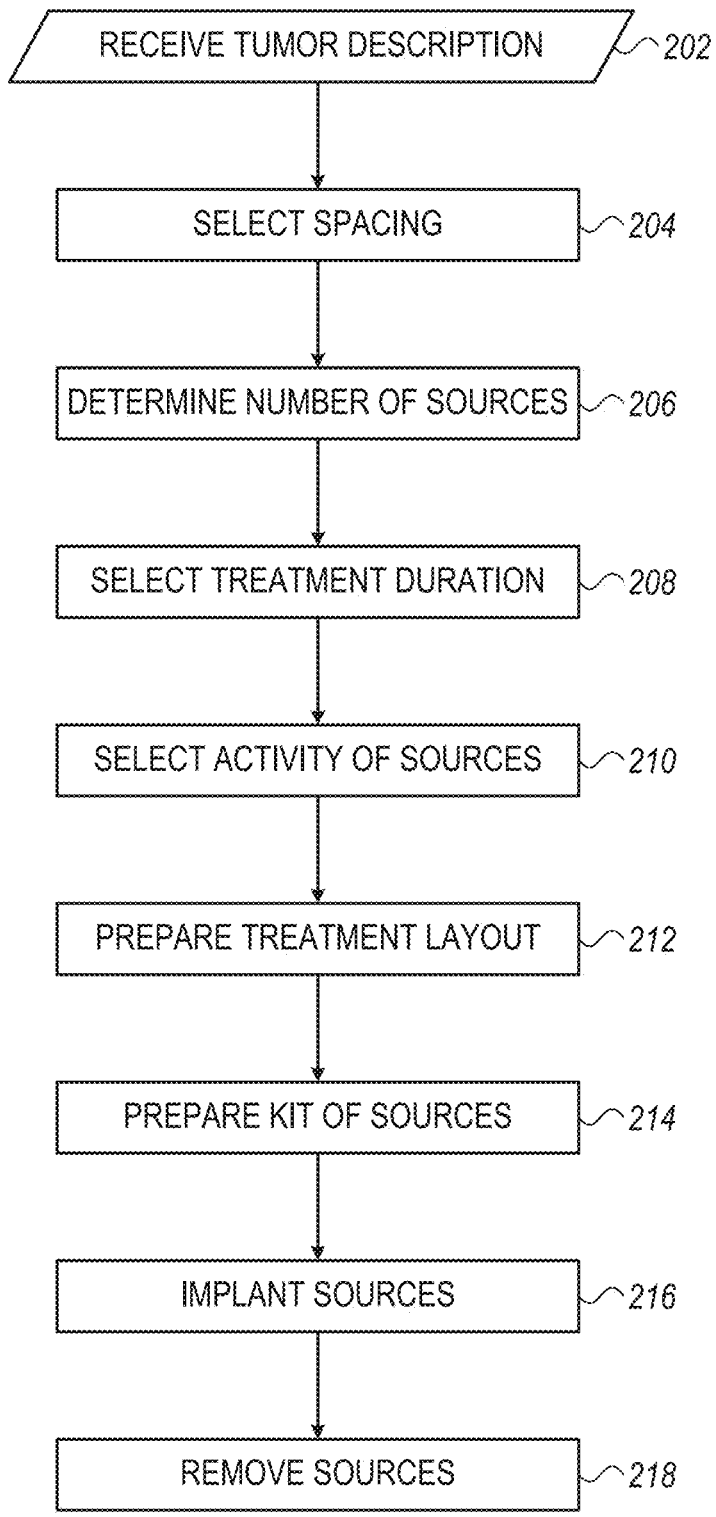
FIG. 2 is a flowchart of acts performed in preparing a radiotherapy treatment of a tumor, in accordance with an embodiment of the invention.

FIG. 2 is a flowchart of acts performed in preparing a radiotherapy treatment of a tumor, in accordance with an embodiment of the invention. The method of FIG. 2 generally begins with system 100 receiving (202) input on the tumor such as an image of the tumor and/or a type of the tumor. A spacing between the sources to be inserted to the tumor is selected (204) for the tumor and accordingly a number of sources to be included in a treatment kit for the tumor is determined (206). In addition, a duration of the treatment is selected (208). The radon release rate of the sources is also selected (210). In some embodiments, instructions on a layout of the sources in the tumor are also prepared (212). Thereafter, a kit including the number of sources of the selected parameters is prepared (214) and packaged in a suitable sterile package. In some embodiments, the method further includes the treatment procedure. In those embodiments, the method includes implanting (216) the sources from the kit into the tumor, for example in accordance with the prepared (212) layout. In some embodiments, the method includes removing (218) the sources after the selected (208) duration. In other embodiments, the sources are not removed and remain in the patient.

In some embodiments, the type of the tumor is determined based on clinical and/or histopathological observations, such as an analysis of a portion of the tumor taken in a biopsy and/or an amount and/or density of blood vessels in the tumor as determined from an image of the tumor. The type of the tumor is selected, for example, from a list including squamous cell carcinoma, basal cell carcinoma, glioblastoma, sarcoma, pancreatic cancer, lung cancer, prostate cancer, breast cancer and colorectal cancer.

In some embodiments, the sources are arranged in the layout in a regular geometrical pattern which achieves a relatively low distance between each point in the tumor and at least one of the sources.

Figure 3:
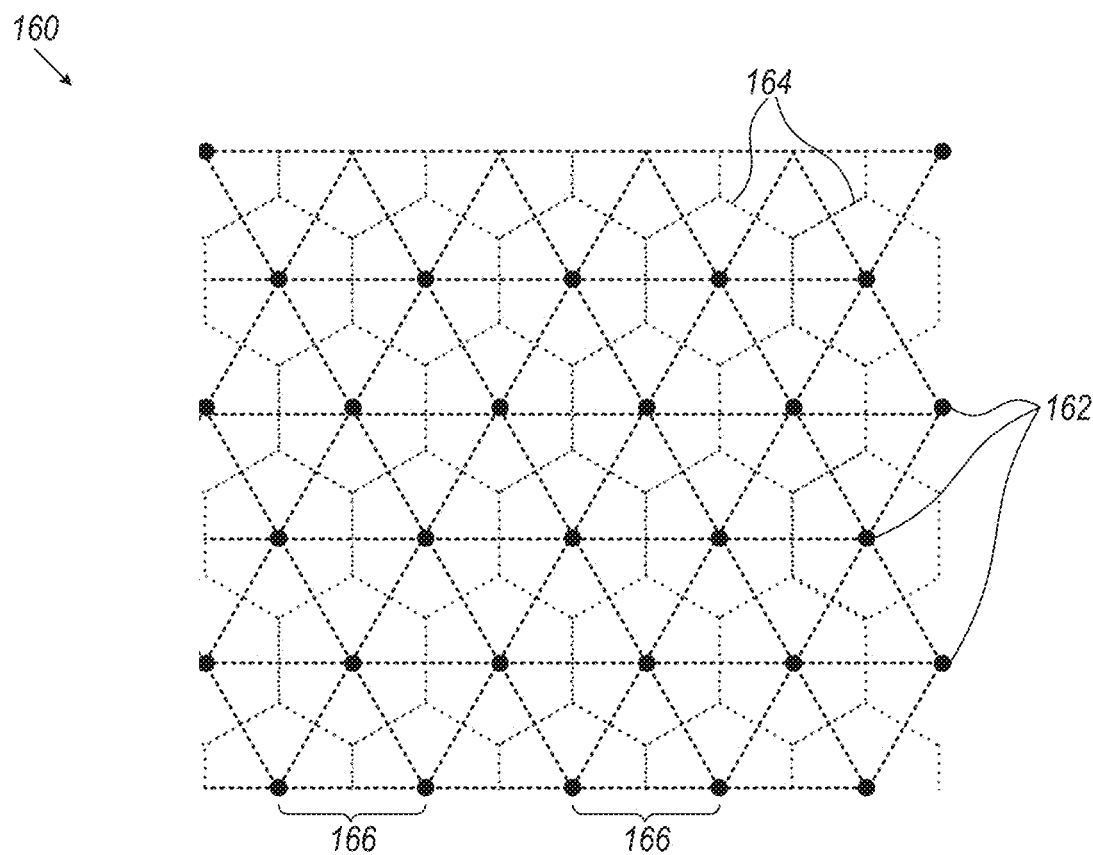
FIG. 3 is a schematic illustration of a regular arrangement of sources in a hexagonal arrangement, in accordance with an embodiment of the invention.

FIG. 3 is a schematic illustration of a regular arrangement of sources in a hexagonal arrangement 160, in accordance with an embodiment of the invention. In hexagonal arrangement 160, a surface through which sources are entered into a tumor to be treated is divided into hexagons 164 and the center 162 of each hexagon is designated for insertion of a source. The centers 162 for insertion of the sources are located at the vertices of equilateral triangles; distance 166 between each two sources is referred to herein as the spacing of the layout. The hexagons 164 are formed by bisectors to the lines connecting the centers 162 to their six nearest neighboring centers 162. The smallest dose of radiation from the sources is at the center of gravity of the triangles, which are at the hexagon vertices. Optionally, the spacing between the sources is smaller than 5 millimeters, not greater than 4.5 millimeters, not greater than 4 millimeters, not greater than 3.5 millimeters, or even not greater than 3 millimeters. The spacing between the sources is highly significant in determining a treatment plan for a specific cancer type, as discussed hereinbelow.

The spacing between the sources is optionally selected (204) as a compromise between the desire to ensure destruction of the tumor without using activity levels which could be close to safety limits, which pushes for a small spacing, and simplicity of the implantation procedure, which pushes for a larger spacing. Generally, the largest spacing which is still believed to destroy the tumor with seeds having an activity level which is not too high, is selected. The spacing is selected (204) responsively to the type of the tumor, because radon-220 and lead-212 have different diffusion lengths in different tumor types, and therefore DaRT sources have different effective ranges in different tumor types. In addition, different tumor types have different required radiation doses. In some embodiments, the spacing is selected (204) according to a type of treatment of the tumor. One type of treatment is directed to complete destruction of the cells of the tumor. Another type of treatment is directed to reduction of the mass of the tumor to a size that is not visible by a naked eye, or to a size that will make the tumor resectable. Complete destruction generally requires a higher activity level of the sources and/or a smaller spacing between the sources.

Alternatively or additionally, in selecting (204) the spacing, the accessibility of the location of the tumor within the patient's body is taken into consideration. For example, for tumors in internal organs which need to be accessed by a catheter or an endoscope, a larger spacing is preferred than for similar tumors which are easily accessed. In some embodiments, the spacing between the sources is selected while taking into consideration the time and complexity of implantation of the sources. The smaller the spacing, the more sources are required and accordingly the time of implantation of the sources increases. Therefore, in accordance with some embodiments of the invention, the largest spacing that would still allow for destruction of the tumor, is used.

Figure 4:
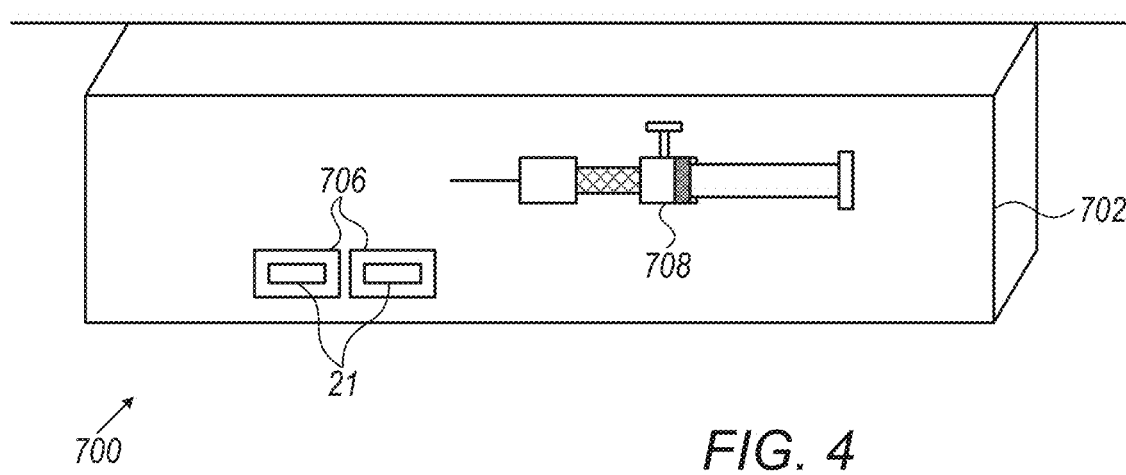
FIG. 4 is a schematic illustration of a kit of DaRT sources, in accordance embodiments of the present invention.

FIG. 4 is a schematic illustration of a kit 700 of DaRT sources 21 in accordance with embodiments of the present invention. Kit 700 comprises a sterile package 702 including a plurality of alpha-emitter radiotherapy sources 21, for insertion into a tumor.

Optionally, the sources 21 are provided within a vial or other casing 706 which prevents radiation from exiting the casing. In some embodiments, the casing is filled with a viscous liquid, such as glycerine, which prevents radon atoms from escaping the casing 706, such as described in PCT application PCT/IB2019/051834, titled "Radiotherapy Seeds and Applicators", the disclosure of which is incorporated herein by reference. In some embodiments, kit 700 further includes a seed applicator 708, which is used to insert sources 21 into the patient, as described in PCT application PCT/IB2019/051834. Optionally, applicator 708 is provided preloaded with one or more sources 21 therein. In accordance with this option, separate sources 21 in casings 706 are supplied for cases in which more than the number of preloaded sources is required. Alternatively, sources 21 in casings 706 are not provided in kit 700 and only sources within applicator 708 are included in the kit 700.

The number of sources to be included in a treatment kit 700 for the tumor is determined (206) according to the selected spacing and source layout, in order to cover the entire tumor. In some embodiments, an extra 10-20% sources are provided in the treatment kit.

The duration of the treatment (e.g., the time that the seeds remain in the tumor) is optionally selected by the operator, according to a desired treatment (e.g., complete destruction, mass reduction). In some embodiments, the duration of the treatment is selected (208) in advance based on parameters of the tumor such as its location in the patient's body and the availability of the patient for removal of the sources. Alternatively, the duration of the treatment is selected (208) during the treatment, based on the progress of the treatment.

The activity of the sources and their desorption probability are optionally selected (210) responsive to the selected spacing, the treatment duration and the tumor type. In some embodiments, the activity of the sources and their desorption probability are further selected responsive to a type of treatment of the tumor. If, for example, an operator indicates that a complete destruction of the cells of the tumor is to be aimed for, a higher activity and/or desorption probability is used than for an indication that a removal of the tumor from naked eye surveillance, or a reduction of the tumor size to make it resectable, is required. Optionally, the activity and source probability are selected with an aim to achieve at least a specific radiation dose at each point throughout the tumor (or at least at above a threshold percentage of points throughout the tumor), according to the type of the tumor, as discussed in more detail below.

It is noted that while the risk of an overdose of radiation for a single small tumor is low, when treating large tumors and/or multiple tumors, the treatment may include implantation of several hundred sources. In such cases, it is important to accurately adjust the activity of the sources to prevent administering an overdose of radiation to the patient. It is generally considered undesirable to implant in a patient an activity level of more than several (e.g., 2-5) millicurie. However, to be on the safe side, a limit of about 1 millicurie is currently used. For a large tumor requiring 170 centimeters or more of seeds, this sets a limit of about 6 microcurie on the activity of a single centimeter length of a seed. In terms of radon release rate, given a desorption rate of 38-45%, this sets a limit of about 2.5 microcurie. This limit is not the same for all tumor types. Some tumor types, such as glioblastoma multiforme (GBM), prostate, breast and squamous cell carcinoma, are generally expected to be treated by radiation when they are small. Therefore, the number of seeds used and their total length are expected to be smaller than 170 cm, so that higher radon release rates may be used. Other cancer types, such as pancreas, are expected to require radiation treatment for large tumors. Further cancer types, such as melanoma and colorectal, are expected to require radiation treatment for several different tumors. These cancer types may require seeds at a total length of 170 cm or even more.

It is noted that the acts of FIG. 2 are not necessarily performed in the order in which they are presented. For example, in cases in which the activity of the sources is not selected (210) responsive to the treatment duration, the activity of the sources may be selected (210) before, or in parallel to, selecting (208) the treatment duration. As another example, the preparation of the layout and the preparation of the kit may be performed concurrently or in any desired order.

Figure 5:
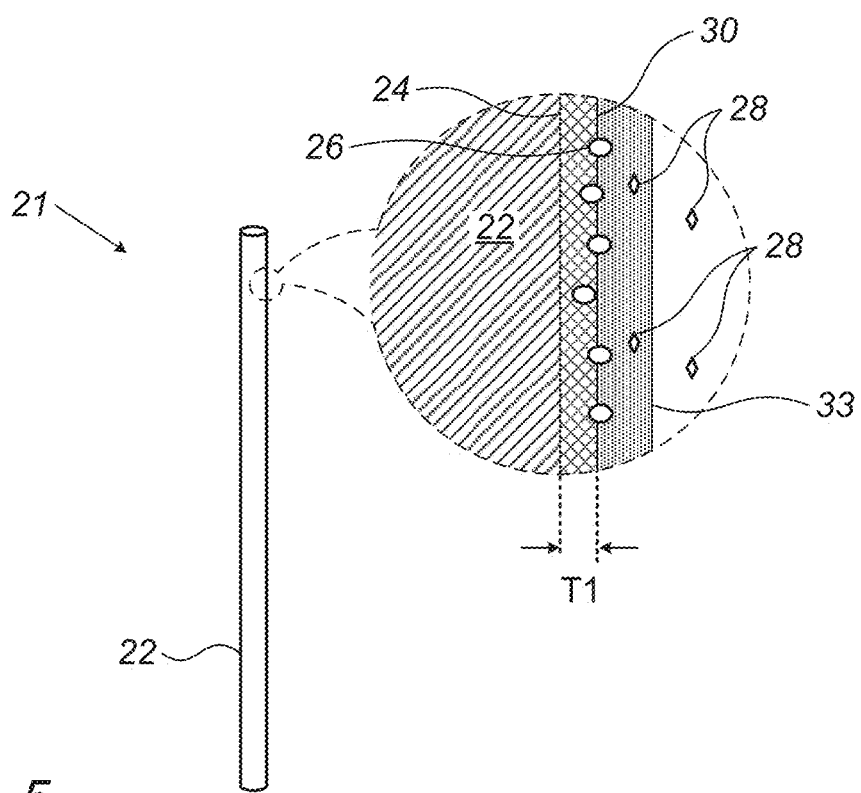
FIG. 5 is a schematic illustration of a radiotherapy source, in accordance with an embodiment of the present invention.

FIG. 5 is a schematic illustration of a radiotherapy source 21, in accordance with an embodiment of the present invention. Radiotherapy source 21 comprises a support 22, which is configured for insertion into a body of a subject. Radiotherapy source 21 further comprises radionuclide atoms 26 of radium-224 on an outer surface 24 of support 22, as described, for example, in U.S. Pat. No. 8,894,969, which is incorporated herein by reference. It is noted that for case of illustration, atoms 26 as well as the other components of radiotherapy source 21, are drawn disproportionately large. Atoms 26 are generally coupled to support 22 in a manner such that radionuclide atoms 26 do not leave the support, but upon radioactive decay, their daughter radionuclides, shown symbolically as 28, may leave support 22 due to recoil resulting from the decay. The percentage of daughter radionuclides 28 that leave the support due to decay is referred to as the desorption probability. The coupling of atoms 26 to support 22 is achieved, in some embodiments, by heat treatment. Alternatively or additionally, a coating 33 covers support 22 and atoms 26, in a manner which prevents release of the radionuclide atoms 26, and/or regulates a rate of release of daughter radionuclides 28, upon radioactive decay. Daughter radionuclides may pass through coating 33 and out of radiotherapy source 21 due to recoil or the recoil may bring them into coating 33, from which they leave by diffusion. In some embodiments, as shown in FIG. 5, in addition to coating 33, an inner coating 30 of a thickness T1 is placed on support 22 and the radionuclide atoms 26 are attached to inner coating 30. It is noted, however, that not all embodiments include inner coating 30 and instead the radionuclide atoms 26 are attached directly to support 22.

Support 22 comprises, in some embodiments, a seed for complete implant within a tumor of a patient, and may have any suitable shape, such as a rod or plate. Alternatively to being fully implanted, support 22 is only partially implanted within a patient and is part of a needle, a wire, a tip of an endoscope, a tip of a laparoscope, or any other suitable probe.

In some embodiments, support 22 is cylindrical and has a length of at least 1 millimeter, at least 2 millimeters, or even at least 5 millimeters. Optionally, the seeds have a length of between 5-60 mm (millimeters). Support 22 optionally has a diameter of 0.7-1 mm, although in some cases, sources of larger or smaller diameters are used. Particularly, for treatment layouts of small spacings, support 22 optionally has a diameter of less than 0.7 mm, less than 0.5 mm, less than 0.4 mm or even not more than 0.3 mm.

The activity on support 22 is measured herein in units of microcurie per centimeter length of the source. As the radiation dose reaching most of the tumor is dominated by radionuclides that leave the source, a measure of "radon release rate" is defined herein as the product of activity on the source and desorption probability. For example, a source with 2 microcurie activity per centimeter length and a 40% desorption probability has a radon release rate of 0.8 microcurie per centimeter length.

The desorption probability depends on the depth of radionuclide atoms 26 within the surface of support 22 and/or on the type and thickness of coating 33. The implanting of the radionuclide atoms 26 in the surface of support 22 is generally achieved by heat treatment of the radiotherapy device 21, and the depth of atoms 26 is controllable by adjusting the temperature and/or duration of the heat treatment. In some embodiments, the desorption probability is between about 38-45%. Alternatively, higher desorption probabilities are achieved, for example using any of the methods described in PCT publication WO 2018/207105, titled: "Polymer Coatings for Brachytherapy Devices", the disclosure of which is incorporated herein by reference. In other embodiments, lower desorption probabilities are used, such as described in US provisional patent application 63/126,070, titled: "Diffusing Alpha-emitters Radiation Therapy with Enhanced Beta Treatment", the disclosure of which is incorporated herein by reference.

It is noted that not all the alpha radiation that reaches the tumor is due to daughter radionuclides 28 of radon-220 that leave the support 22 upon decay. Some of the daughter radionuclides 28 of radon-220 generated from decay of radionuclide atoms 26, remain on support 22. When the daughter radionuclides 28 decay, their daughter radionuclides, e.g., polonium-216, may leave the support 22 due to recoil, or lead-212 generated upon decay of polonium-216 may leave support 22 due to recoil.

Generally, radionuclide atoms 26 are coupled to support 22 in a manner which prevents the radionuclide atoms 26 themselves from leaving support 22. In other embodiments, radionuclide atoms 26 are coupled to support 22 in a manner which allows radionuclide atoms 26 to leave the support without decay, e.g., by diffusion, for example using any of the methods described in PCT publication WO 2019/193464, titled: "Controlled Release of Radionuclides", which is incorporated herein by reference. The diffusion is optionally achieved by using a bio-absorbable coating which initially prevents premature escape of radionuclide atoms 26 but after implantation in a tumor disintegrates and allows the diffusion.

The total amount of radiation released by a source in a tumor, referred to herein as "cumulated activity of released radon", depends on the radon release rate of the source and the time for which the source remains in the tumor. If the source is left in the tumor for a long period, for example more than a month for a radium-224 source, the cumulated activity of released radon reaches the product of radon release rate of the source multiplied by the mean life time of radium-224, which is 3.63 days or 87.12 hours, divided by ln 2, which is about 0.693. For example, a radium-224 source having a radon release rate of 1 microCurie (μCi) =37.000 becquerel (Bq), has a cumulated activity of released radon of about 4.651 Mega becquerel (MBq) hour. It is noted that the same amount of cumulated activity of released radon may be achieved by implanting a source with a higher radon release rate for a shorter period. For such a shorter period, the cumulated activity is given by:

$$\text{cumulated activity} = S(0) * \tau * \left(1 - e^{-\frac{t}{\tau}}\right)$$

where $S(0)$ is the radon release rate of the source when it is inserted into the tumor, $\tau$ is the mean radium-224 lifetime and t is the treatment duration in hours. For example, a two-week treatment provides a cumulated activity of:

$$\text{cumulated activity (14 days)} =$$
$$0.037 \ MBq * 125.7 \ h * \left(1 - e^{-14 * \frac{24}{125.7}}\right) = 4.330 \ MBqh$$

The required amount of activity on the sources in order to achieve tumor destruction varies dramatically for different types of tumors and source spacings. It is therefore important to identify for each type of tumor, the required activity for that specific tumor type. Methods for calculating the radiation dose reaching each point in a tumor, according to the activity of the implanted sources, are described in U.S. patent application Ser. No. 17/141,251, filed Jan. 5, 2021 and titled, "Treatment Planning for Alpha Particle Radiotherapy", the disclosure of which is incorporated herein by reference. Using those calculation methods, the required radon release rate can be calculated as a function of the diffusion length of lead-212 in the tumor, the diffusion length of radon-220 in the tumor, the spacing between the sources implanted in the tumor, the leakage probability of lead-212 from the tumor and the radiation dose required to reach each location in the tumor.

Figure 6A:
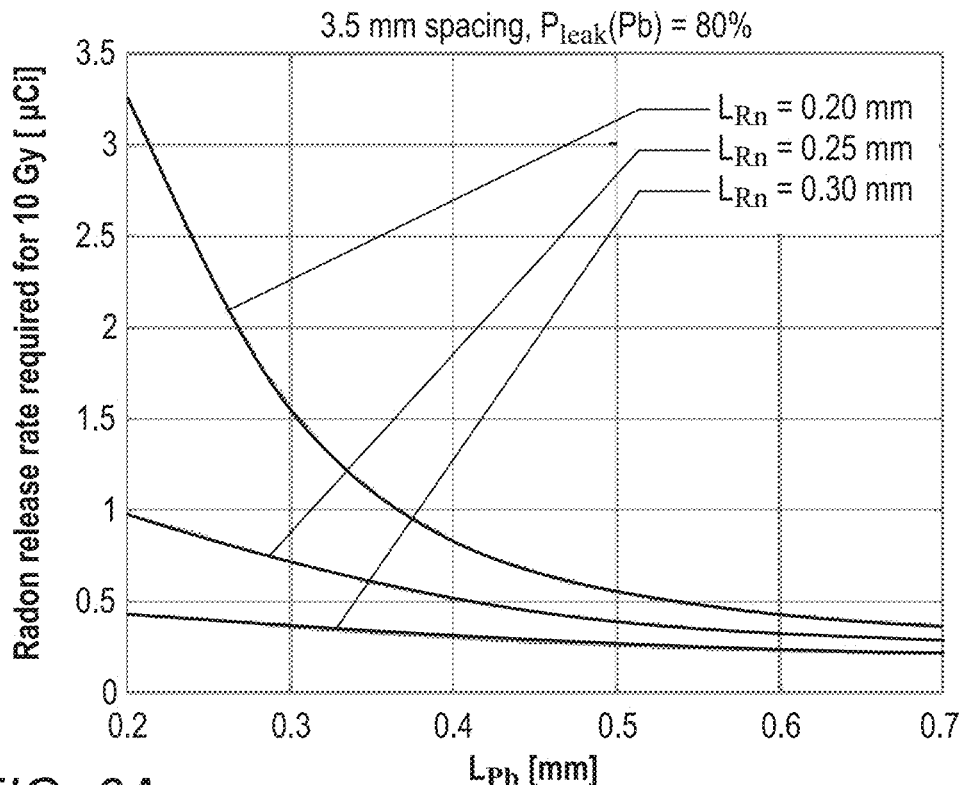
FIGS. 6A-6D are graphs which illustrate the wide range of radon release rate values, required to ensure a nominal alpha-particle dose of at least 10 Gray (Gy), for different seed spacings, lead-212 leakage probabilities and radon-220 and lead-212 diffusion lengths.
Figure 6B:
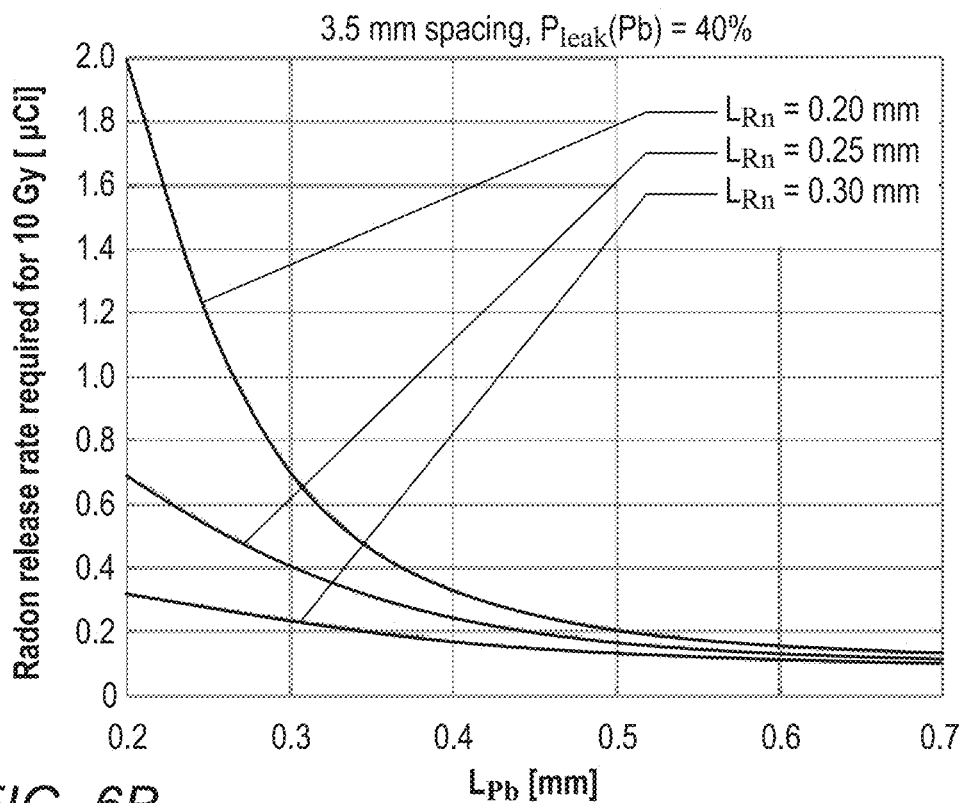
Figure 6C:
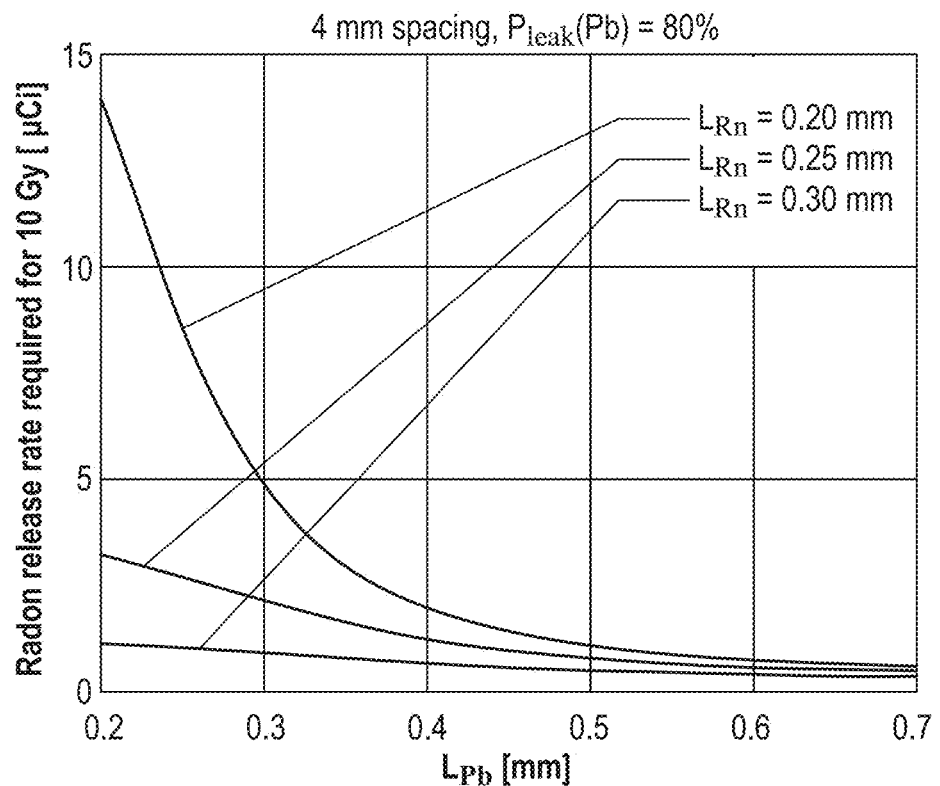
Figure 6D:
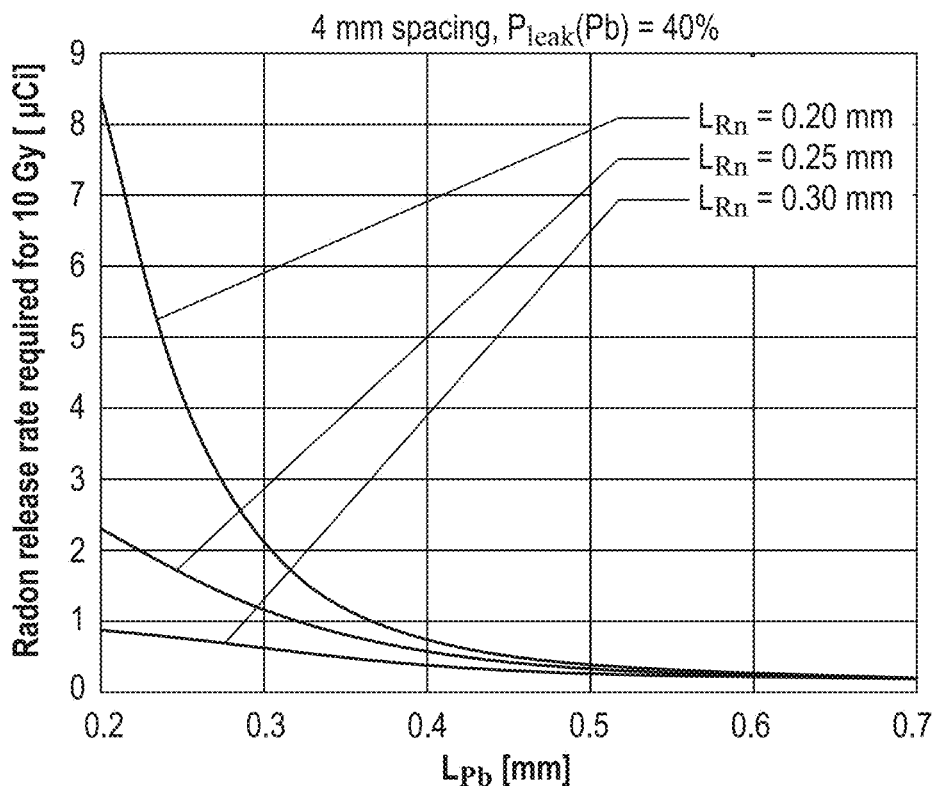

FIGS. 6A-6D are graphs which illustrate the wide range of radon release rate values, required to ensure a nominal alpha-particle dose of at least 10 Gray (Gy), for different values of the above parameters. The 10 Gy level is chosen as a reference, as the nominal alpha particle dose required depends on the tumor type and can be as high as 20-30 Gy. To get the required seed activity for a target dose other than 10 Gy, the seed activity for 10 Gy should be multiplied by the ratio between the target dose and 10 Gy. FIG. 6A shows the required radon release rate as a function of the lead-212 diffusion length, for three different values of the radon-220 diffusion length, when the lead leakage probability is 80% and the spacing is 3.5 mm. FIG. 6B is a similar graph, for a lead leakage probability of 40%. FIG. 6C shows the same graph for a spacing of 4 mm and lead leakage probability of 80%, while FIG. 6D shows the required radon release rate for 4 mm spacing and 40% lead leakage probability. The reader will appreciate that the range of possible radon release rate values is very large and the following discussion provides guidance as to narrow ranges to be used for specific tumor types.

Figure 6E:
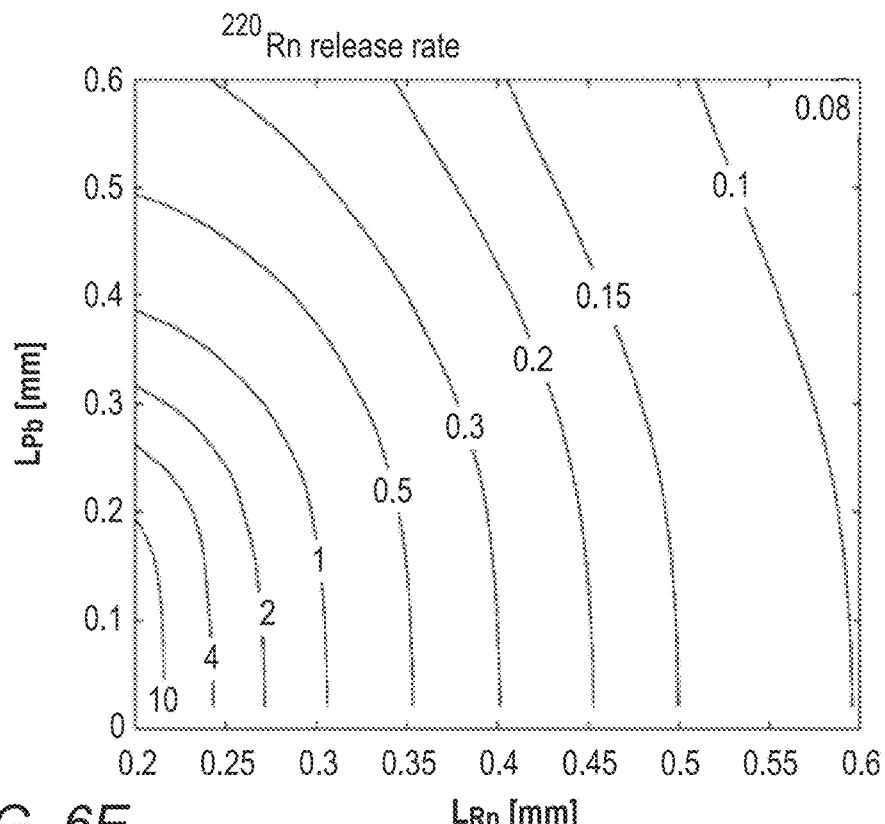
FIG. 6E is a contour graph showing the value of the required radon release rate for a 4 mm spacing, 50% lead-212 leakage, and a radiation dose of 10 Gy, for various possible radon-220 and lead-212 diffusion lengths over a range of interest, in accordance with embodiments of the invention.

FIG. 6E is a contour graph showing the value of the required radon release rate for a 4 mm spacing, 50% lead-212 leakage, and a radiation dose of 10 Gy, for various possible radon-220 and lead-212 diffusion lengths over a range of interest, in accordance with embodiments of the invention.

Figure 6F:
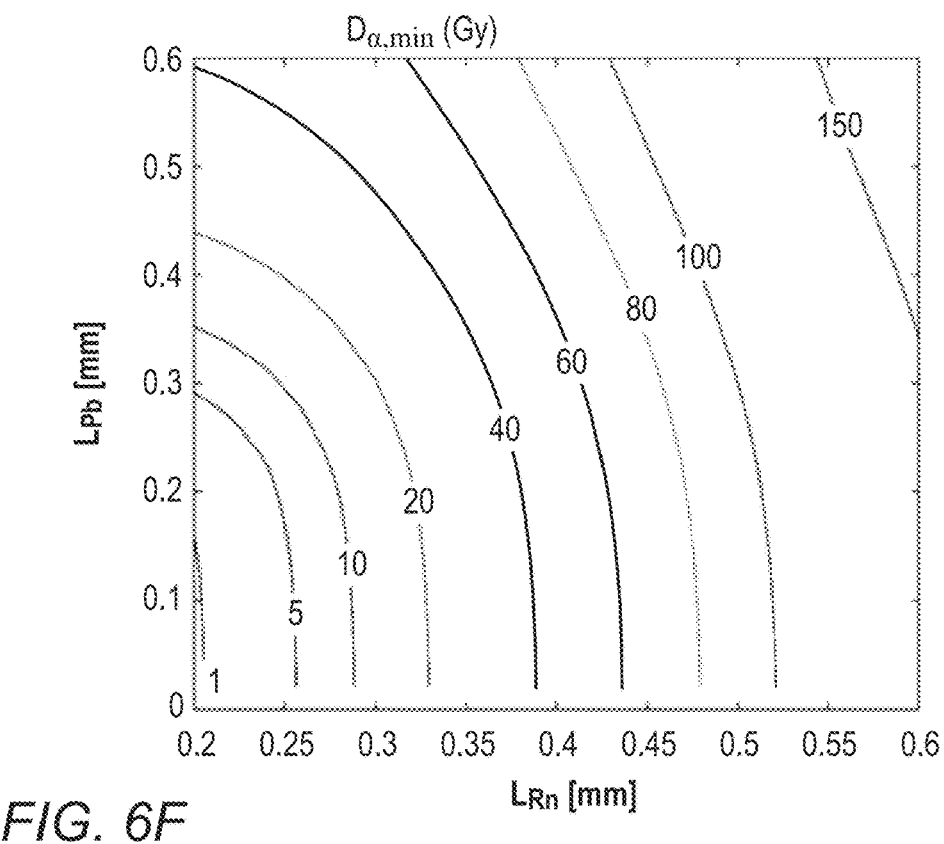
FIG. 6F is a contour graph showing the minimal radiation dose expected to reach the cells of a tumor in which seeds of 3 microcurie per cm length are implanted at a 4 mm spacing, assuming 50% lead-212 leakage, for various possible radon-220 and lead-212 diffusion lengths, in accordance with embodiments of the invention.

FIG. 6F is a contour graph showing the minimal radiation dose expected to reach the cells of a tumor in which seeds of 3 microcurie per cm length are implanted at a 4 mm spacing, assuming 50% lead-212 leakage, for various possible radon-220 and lead-212 diffusion lengths, in accordance with embodiments of the invention.

As can be seen in FIG. 6E, the required radon release rate varies substantially for different diffusion lengths. As different tumor types have different diffusion lengths, the required radon release rate is different for different tumor types.

In order to estimate the diffusion length of lead-212 and the diffusion length of radon-220 in different types of tumors, applicant performed two classes of experiments, on various types of tumors and on tumors of various sizes. In a first experiment class, applicant implanted sources inside tumors generated in mice and after a few days dissected the tumor and measured the actual activity that reached the various points in the tumor. These measurements are fit into the above equations and accordingly an effective long-term diffusion length in the tumor is estimated. This effective diffusion length is the larger of the diffusion lengths of radon-220 and lead-212.

The tumor was removed from the mouse and frozen so that the tumor can be sliced a short time after the removal of the tumor from the mouse. Thereafter, the tumor was cut into slices of a thickness of about 10 microns. Fixation by formalin was done immediately after sectioning, and for a short duration (minutes), directly on the histological slices, placed on glass slides. After fixation, the slides were laid on a Fuji phosphor imaging plate in closed box for one hour. The slides were separated from the plate by a thin Mylar foil to avoid contaminating the plate by radioactivity. The plate was subsequently scanned by a phosphor imaging autoradiography system (Fuji FLA-9000) to record the spatial distribution of lead-212 inside the histological slices.

Further details of the measurement of the effective long-term diffusion length are discussed hereinbelow in appendix A.

The second class of experiments is similar to the first class, but rather than waiting several days, the tumor was removed about half an hour after source insertion. The distribution of radioactivity after such a short duration is believed to be predominantly due to diffusion of radon-220, as the spatial distribution of radon-220 stabilizes very fast, while the contribution arising from lead-212 increases from zero to a maximal value about 1.5-2 days after source insertion, and is sufficiently low 30 minutes after source insertion. Details of the measurement of the diffusion length of radon-220 are discussed hereinbelow in appendix B.

Early measurements of the diffusion length of radon-220 found values of between 0.23 and 0.31 mm. The number of measurements, however, was relatively small. Recent results of the above described measurements showed, surprisingly, no significant difference between the long-term and short-term experiments. Applicant therefore postulates that the diffusion length of lead-212 is smaller than the diffusion length of radon-220. Applicant is therefore assuming that the lead-212 is about 0.2 millimeters. This assumption is being used because, as can be seen in FIG. 6E, the dependence on the lead-212 diffusion length is weak in the range of values of the diffusion length of radon-220. The measured radon-220 diffusion lengths are summarized for a plurality of cancer types in the following table 1.

As is known in the art, different tumor types require different doses of radiation for destruction of their cells. Table 1 includes the required biological effective dose (BED) of various types of cancer tumors in Gray equivalent (GyE). These dose values are for photon-based radiation (x-, or gamma-rays). Alpha radiation is considered more lethal to cells, and therefore the dose of alpha radiation in Gray is multiplied by a correction factor known as relative biological effect (RBE), currently estimated as 5, to convert it to BED in Gray equivalent (GyE). The BED in DaRT is the sum of the alpha dose multiplied by the RBE and the beta dose arising from radium-224 and its daughters.

The lead-212 leakage probability is relatively low in the center of the tumor, but reaches about 80% on the periphery of the tumor. In order to ensure cell destruction throughout the tumor, applicant has used the 80% leakage probability value in selecting the radon release rate of the sources.

In order to estimate the desired spacing and radon release rate of the seeds for a specific tumor type, applicant estimates the required dose for the tumor type, the beta radiation dose provided by a span of activity levels, and a remaining required dose that needs to be provided by the alpha radiation. The alpha radiation dose is estimated for a span of spacings and radon release rates and a safety factor which is the ratio between the estimated provided dose and the required dose is calculated for the span of spacings and radon release rates. The safety factor is required to overcome inaccuracies which may occur in the placement of the sources, such that some sources may be separated by an extent larger than the prescribed spacing. In addition, the tumor may be non-homogenous with some local variations in the diffusion lengths.

Applicant has selected the safety factor range of between 1.5-4 as defining the desired spacing and radon release range for treatment. This safety factor is believed to provide sufficient safety that the tumor will be destroyed by the provided radiation, while not being too high to risk the patient from systemic radiation, arising from the leakage of lead-212 from the tumor through the blood and subsequent uptake in various organs.

For a given tumor type, the same safety factor can be achieved with different pairs of spacings and radon release rates. If the sources are to be placed with a relatively high spacing between them, such as 4.5 mm or 5 mm, the sources should have a high radon release rate, such as above 1.5 microcurie per centimeter length. In contrast, when the spacing between the sources is below 4 mm, the sources may be assigned a relatively low radon release rate.

Given the selected safety factor range, a suitable source spacing is selected. As stated above, the largest spacing which is still believed to destroy the tumor with seeds having an activity level which is not too high, is selected. Applicant is limiting the election of spacings to steps of 0.5 millimeters, which is believed to be close to a level of inaccuracy in seed placement. These inaccuracies are taken into consideration in the safety factor.

After selecting the spacing, a range of radon release rates corresponding to the spacing and to the safety factor is selected. This range of radon release rates is believed to provide best results in treating tumors of the tumor type for which the calculations were performed. It is noted that the selected range of radon release rates is not limited to use with the specific spacing used to select the range, but rather can be used, due to the safety margin, with a range of spacings surrounding the selected spacing.

TABLE 1

| Tumor type | Effective long-term diffusion length in millimeters (all sizes) | Required dose (Biological effective dose (BED) in Gray equivalent) |
|---|---|---|
| Squamous cell carcinoma | 0.44 | 60 |
| Colorectal | 0.44 | 120 |
| Glioblastoma (GBM) | 0.27 | 100 |
| Melanoma | 0.40 | 150 |
| Prostate | 0.32 | 173 |
| Breast (triple negative) | 0.35 | 60 |
| Pancreatic cancer | 0.29 | 100 |

As stated in Table 1, the effective long-term diffusion length for melanoma is estimated to be about 0.4 mm and the required dose is about 150 GyE.

Table 2 presents the beta dose, the corresponding required alpha radiation dose, the estimated alpha radiation dose and the resulting safety factor, for several spacings and radon release rates for melanoma.

Figure 7:
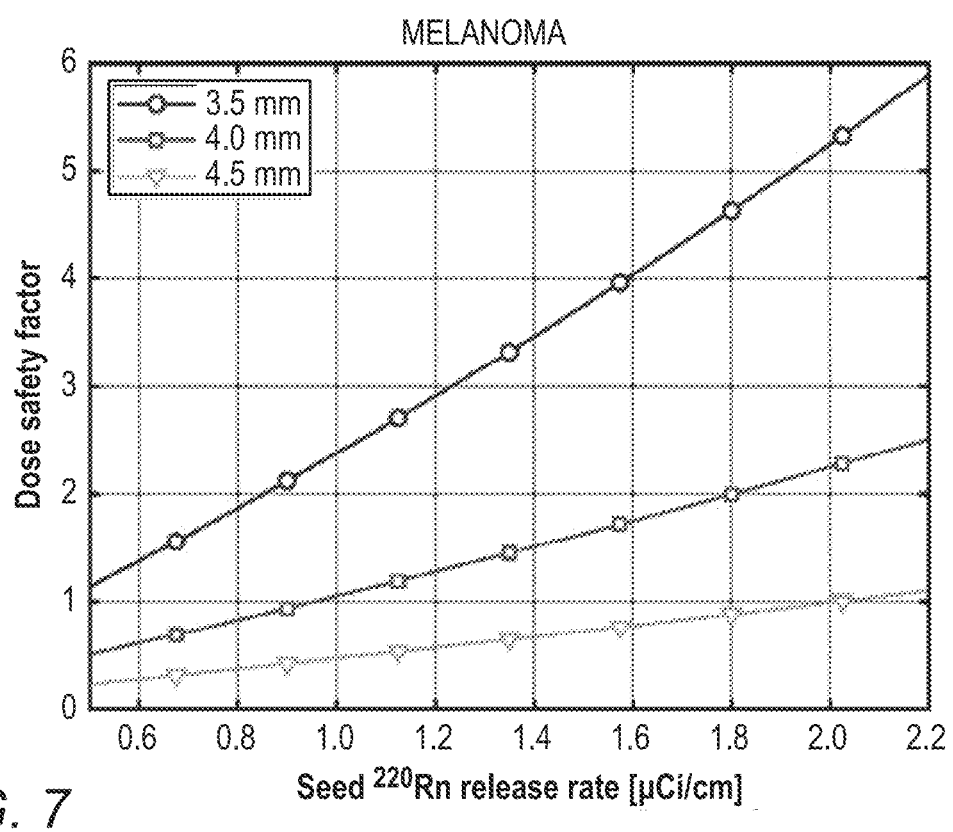
FIG. 7 is a graph which shows a safety factor for various spacings and a range of radon release rates for melanoma, in accordance with embodiments of the present invention.

FIG. 7 is a graph which shows the safety factor as a function of the radon release rate for melanoma for various spacings, in accordance with embodiments of the present invention.

From FIG. 7 applicant determined that a spacing of 4 millimeters would require at the upper portion of the safety factor range of 1.5-4, seeds with a radon release rate considerably above 2.5 microcurie. To avoid such a high activity level, a spacing of 3.5 millimeters is assumed in selecting the radon release rate for the sources. The actual spacing used is optionally shorter than 3.9 millimeters, shorter than 3.8 millimeters, shorter than 3.7 millimeters, or even shorter than 3.6 millimeters. On the other hand, the actual spacing used is optionally greater than 3.1 millimeters, greater than 3.2 millimeters, greater than 3.3 millimeters, or even greater than 3.4 millimeters.

TABLE 2

| | | Melanoma | | |
|---|---|---|---|---|
| | | Spacing (mm) | | |
| | | 3 | 3.5 | 4 |
| Beta dose | 0.9 µCi | 16.3 | 11.5 | 8.0 |
| | 1.35 µCi | 24.4 | 17.3 | 12.0 |
| | 1.8 µCi | 32.6 | 23.1 | 16.0 |
| Required nominal alpha dose | 0.9 µCi | 26.7 | 27.7 | 28.4 |
| | 1.35 µCi | 25.1 | 26.5 | 27.6 |
| | 1.8 µCi | 23.5 | 25.4 | 26.8 |
| alpha dose | 0.9 µCi | 130.9 | 58.7 | 26.6 |
| | 1.35 µCi | 196.4 | 88.1 | 39.9 |
| | 1.8 µCi | 261.9 | 117.4 | 53.2 |
| Safety factor | 0.9 µCi | 4.90 | 2.12 | 0.94 |
| | 1.35 µCi | 7.82 | 3.32 | 1.45 |
| | 1.8 µCi | 11.15 | 4.63 | 1.98 |

For the 3.5 millimeter spacing, a radon release rate of between 0.67-1.6 microcurie per centimeter length is believed to achieve sufficient destruction of the tumor with a high probability, without unnecessarily exposing the patient to unrequired radiation. For a long-term treatment, this corresponds to a cumulated activity of released radon of between about 3.2 MBq hour per centimeter and 7.5 MBq hour per centimeter.

In some embodiments, in order to increase the probability of success of the treatment, a radon release rate of at least 1.0 microcurie per centimeter length, at least 1.2 microcurie per centimeter length, at least 1.4 microcurie per centimeter length or even at least 1.5 microcurie per centimeter length is used for melanoma. On the other hand, in some embodiments, in order to reduce the amount of radiation to which the patient is exposed, the radon release rate is not greater than 1.5, not greater than 1.4 or even not greater than 1.3 microcurie per centimeter length. In other embodiments, a safety factor of between 1.5-2.5 is used, and accordingly the radon release rate is between 0.67 and 1.1 microcurie per centimeter length. In still other embodiments, a safety factor of between 3-4 is used, and accordingly the radon release rate of the seeds 21 is between 1.25 and 1.6 microcurie per centimeter length.

Alternatively or additionally, the sources optionally include at least 3.5 MBq hour per centimeter, at least 4.5 MBq hour per centimeter, at least 5.5 MBq hour per centimeter or even at least 6.5 MBq hour per centimeter. On the other hand, in some embodiments, the sources include less than 7 MBq hour per centimeter or even less than 6.5 MBq hour per centimeter.

CONCLUSION

It will be appreciated that the above described methods and apparatus are to be interpreted as including apparatus for carrying out the methods and methods of using the apparatus. It should be understood that features and/or steps described with respect to one embodiment may sometimes be used with other embodiments and that not all embodiments of the invention have all of the features and/or steps shown in a particular figure or described with respect to one of the specific embodiments. Tasks are not necessarily performed in the exact order described.

It is noted that some of the above described embodiments may include structure, acts or details of structures and acts that may not be essential to the invention and which are described as examples. Structure and acts described herein are replaceable by equivalents which perform the same function, even if the structure or acts are different, as known in the art. The embodiments described above are cited by way of example, and the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art. Therefore, the scope of the invention is limited only by the elements and limitations as used in the claims, wherein the terms "comprise," "include," "have" and their conjugates, shall mean, when used in the claims, "including but not necessarily limited to."

APPENDIX A

Effective Diffusion Length Measurement

A single DaRT seed (6.5 mm length, 0.7 mm outer diameter), carrying 2-3 µCi $^{224}$Ra, is inserted to the center of a mice-borne tumor 7-20 days after tumor inoculation, when the tumor transverse diameter is ~6-15 mm. Four to five days later, the tumor is excised (as a whole) and cut in two halves, at the estimated location of the seed center, perpendicular to the seed axis. The seed is then pulled out using surgical tweezers and placed in a water-filled tube for subsequent measurement by a gamma counter. The tumor is kept for one hour at −80° C. It is then taken, in dry ice, for measurement in the same gamma counter to determine the $^{212}$Pb activity it contains. The measurements of the seed and tumor activity are used to determine the $^{212}$Pb leakage probability from the tumor.

Immediately after the gamma measurement, both halves of the tumor undergo histological sectioning by a cryostat microtome. Sections are cut at 250-300 μm intervals with a thickness of 10 μm, laid on positively charged glass slides and fixed with 4% paraformaldehyde. Typically there are 5-15 sections per tumor, spanning a length of 1.5-5 mm. Shortly after their preparation, the glass slides are placed, faced down, for a duration of one hour, on a phosphor imaging plate (Fujifilm TR2040S) protected by a 12 μm Mylar foil and enclosed in a light-tight casing. Alpha particles emitted from the sections in the decays of $^{212}$Pb progeny atoms, $^{212}$Bi and $^{212}$Po, penetrate through the foil and deposit energy in the active layer of the phosphor imaging plate. The plate is then read out by a phosphor-imaging scanner (Fujifilm FLA-9000).

For each tumor section, the result is a two-dimensional intensity map, proportional to the local $^{212}$Pb activity. The intensity (in units of photo-stimulated luminescence) is converted to $^{212}$Pb activity using suitable calibration samples measured concurrently with the slides. The point where the seed crosses the section is identified either by the appearance of a "hole" in the activity map, or by taking the center-of-gravity of the activity distribution. Examples are shown in FIGS. 8A-8D. We define a region of interest (ROI) centered at the estimated seed location, and divide it into 0.1 mm-wide concentric rings, with radii in the range 0.5-3 mm. For each ring, we calculate the mean value of the activity. If the ROI extends beyond the area of the tumor section, or includes a region with degraded tissue or image quality, the ring average is taken over a limited azimuthal sector. The resulting curve of the activity as a function of the radial distance from the origin (estimated seed location), is then fitted numerically by a function describing the radial activity distribution from a seed, based on the diffusion-leakage model. The calculation describes the seed as a line source perpendicular to the image. The source is divided into a large number of point-like segments, each contributing, to a given pixel in the plane of the image, an activity $$A \frac{\exp(-r/L_{eff})}{r}.$$

In this expression r is the distance between the source segment and the pixel under consideration, and A and $L_{\mathit{ff}}$ are free parameters, whose values are adjusted to optimize the fit to the entire curve (FIGS. 8A-8D). The value obtained for $L_{\mathit{eff}}$ is taken as an estimate for the effective diffusion length of the section. The average value of $L_{\mathit{eff}}$ over all sections is taken to represent the effective (or dominant) diffusion length of the tumor, with an uncertainty equal to the standard deviation of the values obtained in all sections.

Figure 8A:
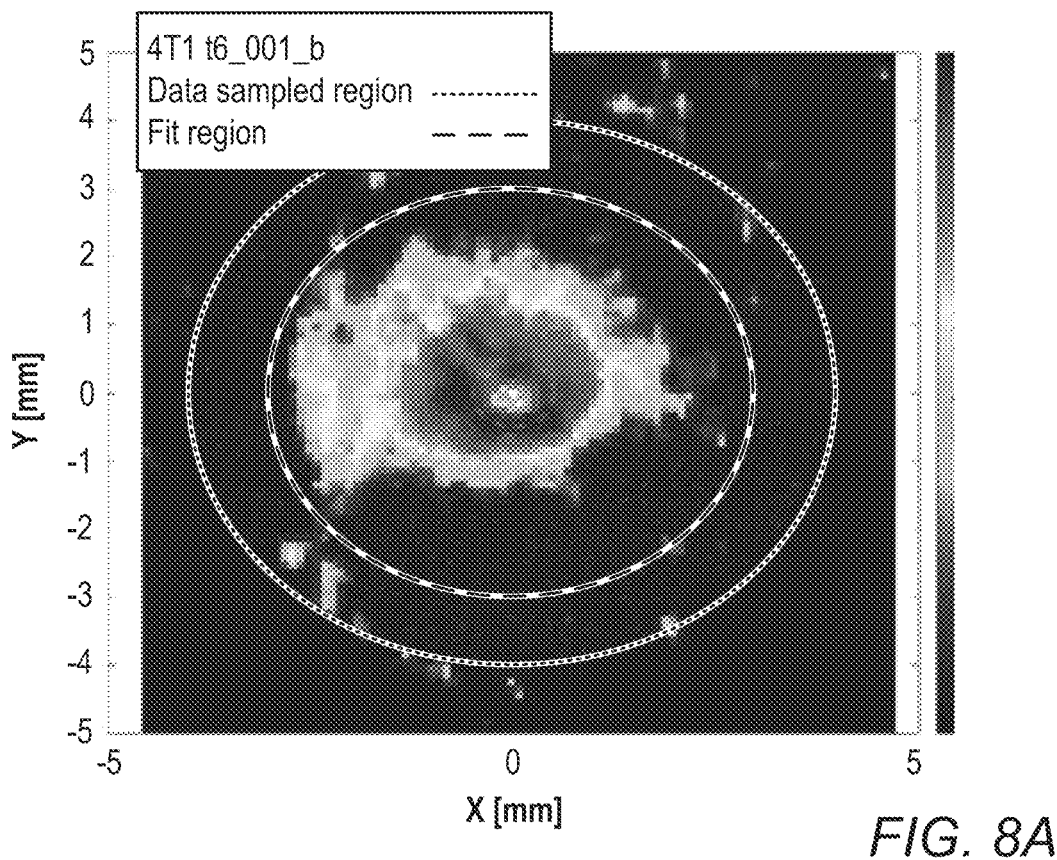
FIG. 8A shows a spatial distribution of the photo-stimulated luminescence (PSL) signal in a histological section of a 4T1 tumor with denoted region of sampled data in white (0-4 mm) and the fit region with magenta dashed line (0.5-3 mm)

FIG. 8A shows a spatial distribution of the photo-stimulated luminescence (PSL) signal in a histological section of a 4T1 tumor with denoted region of sampled data in white (0-4 mm) and the fit region with magenta dashed line (0.5-3 mm). The seed position is determined manually.

Figure 8B:
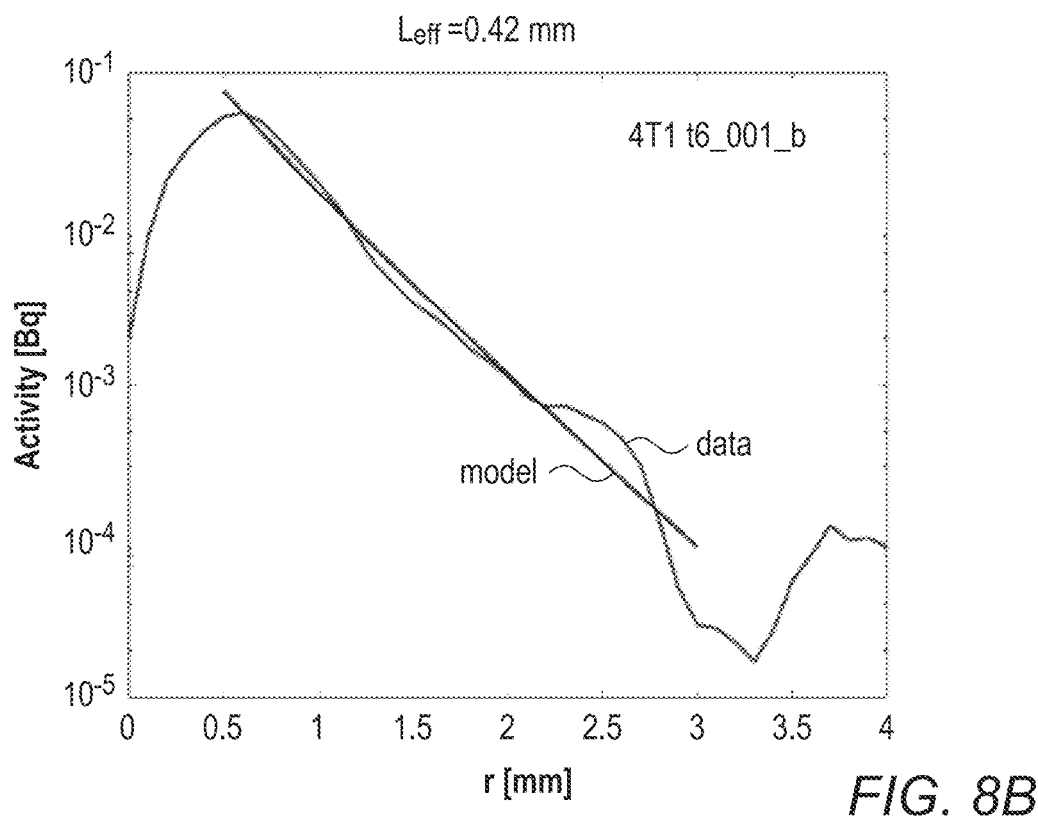
FIG. 8B is a graph of the radial activity distribution for the sampled data of FIG. 8A, fitted by a theoretical model to extract the effective diffusion length.

FIG. 8B is a graph of the radial activity distribution for the sampled data of FIG. 8A, fitted by the diffusion-leakage model.

Figure 8C:
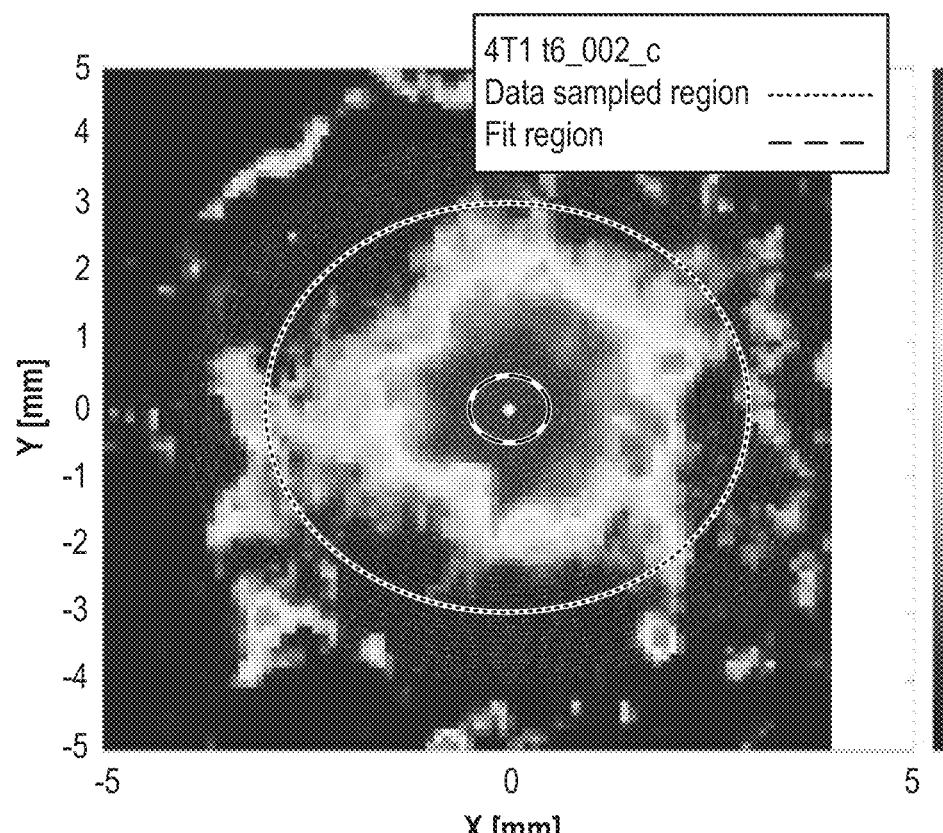
FIG. 8C shows a PSL spatial distribution in another histological section from the same tumor where the seed position is determined automatically by calculating the intensity center-of-gravity.

FIG. 8C shows a PSL spatial distribution in another histological section from the same tumor where the seed position is determined automatically by calculating the intensity center-of-gravity.

Figure 8D:
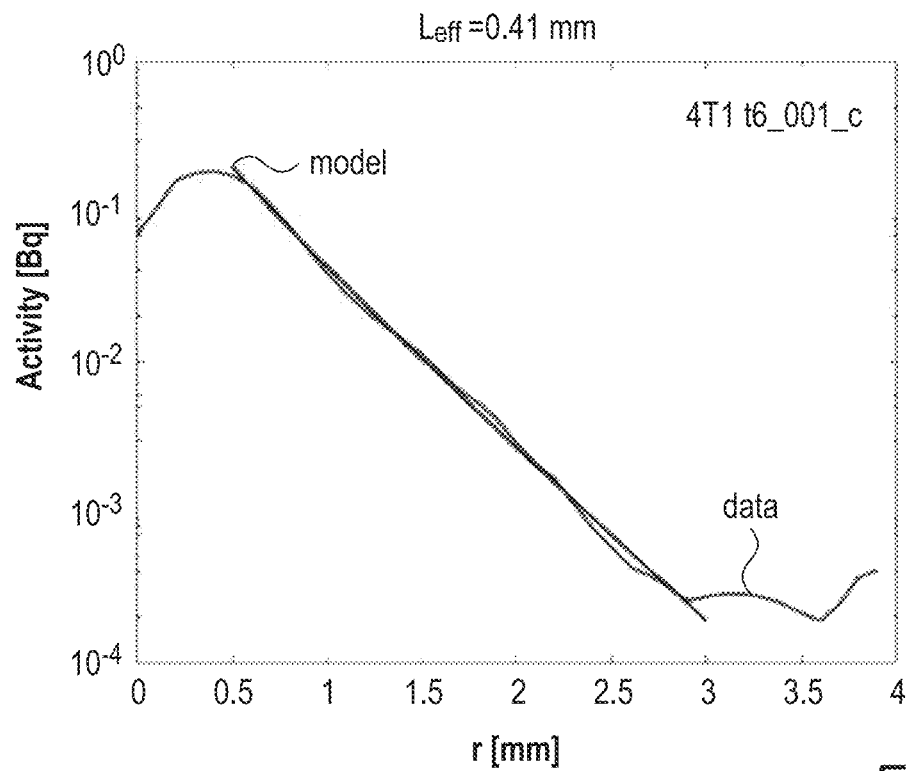
FIG. 8D is a graph of the radial activity distribution for the sampled data of FIG. 8C, fitted by a theoretical model to extract the effective diffusion length.

FIG. 8D is a graph of the radial activity distribution for the sampled data of FIG. 8C, fitted by the diffusion-leakage model.

Figure 9:
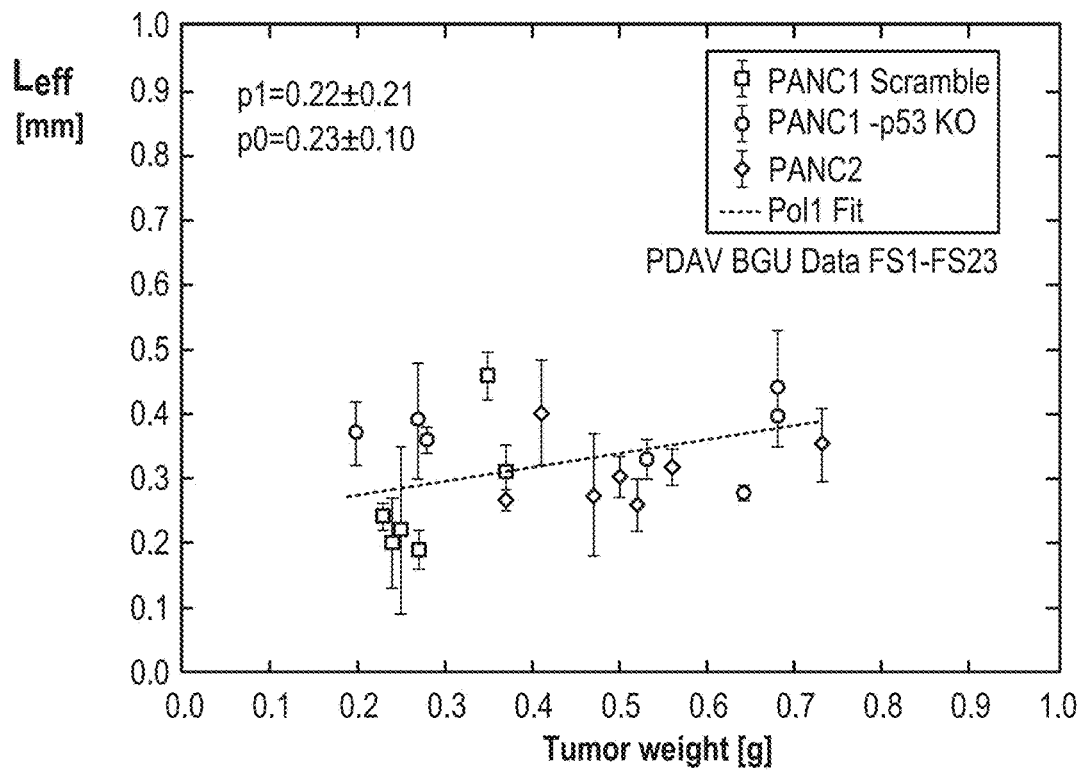
FIGS. 9-14 show the obtained effective diffusion lengths for different tumor types as a function of the tumor mass.

FIG. 9 shows the measured values of the effective diffusion length as a function of tumor mass for pancreatic tumors.

Figure 10:
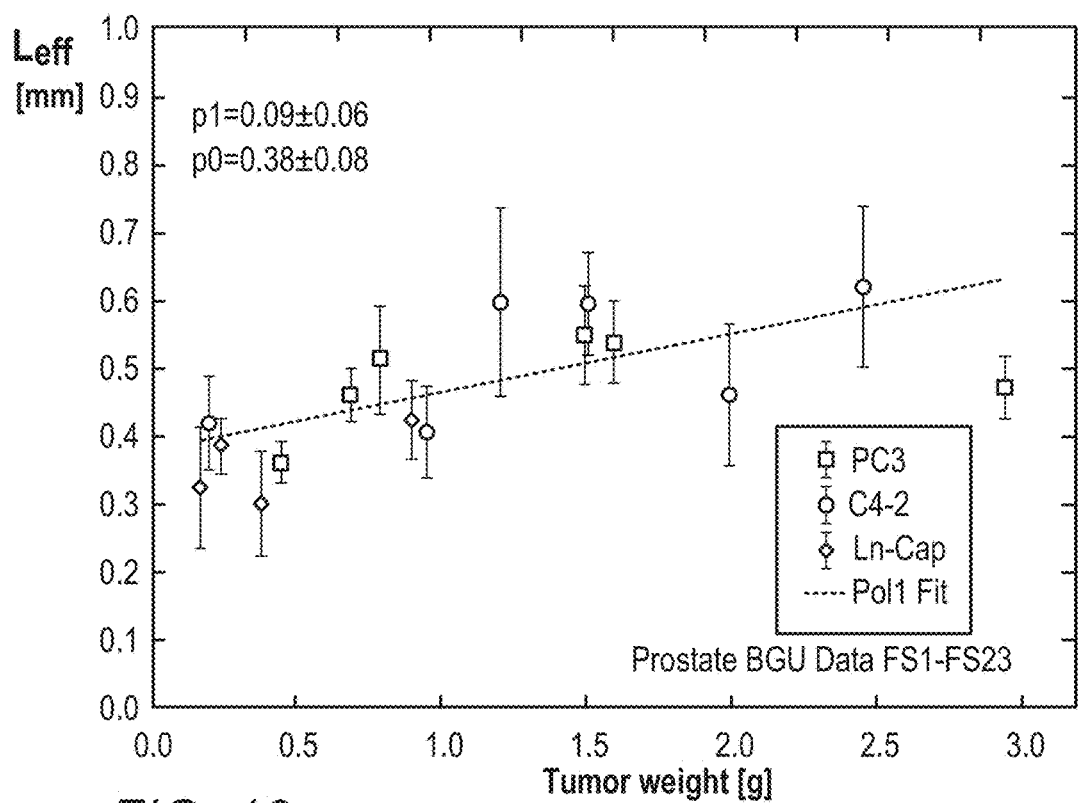

FIG. 10 shows the measured values of the effective diffusion length as a function of tumor mass for prostate tumors.

Figure 11:
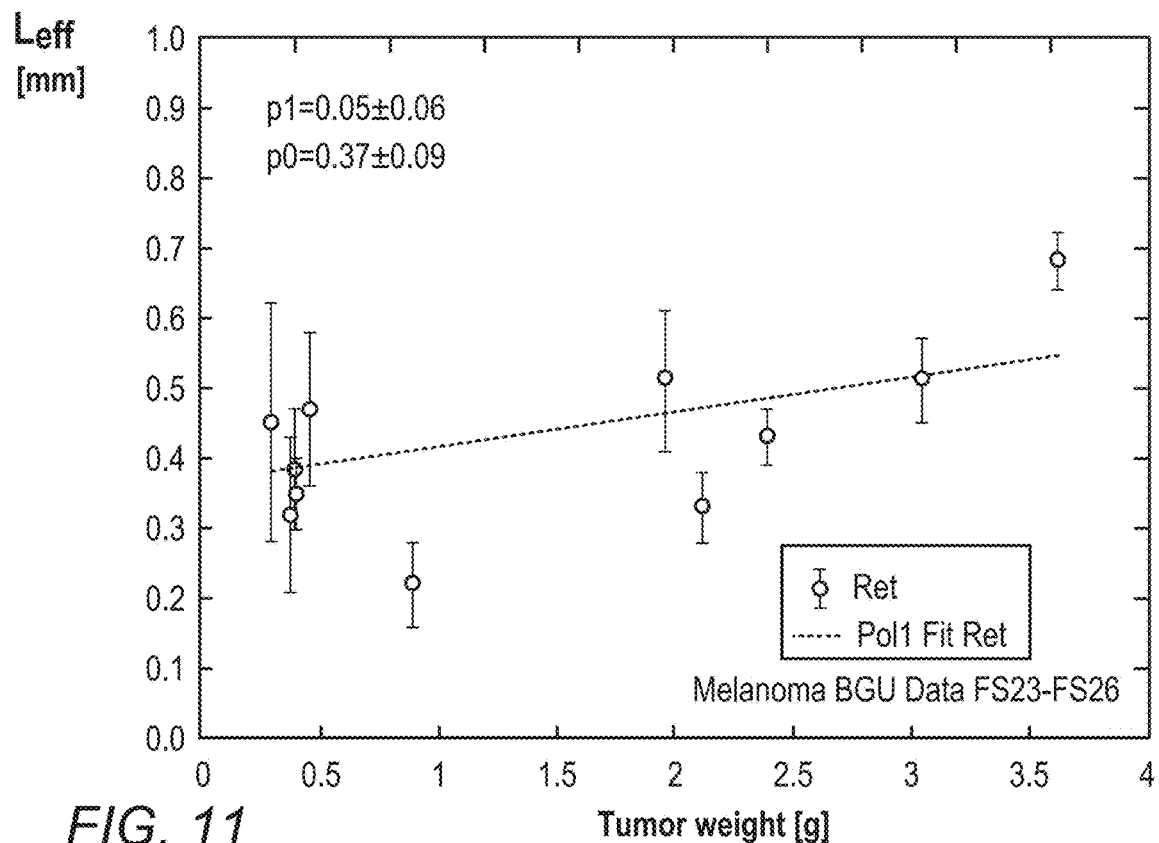

FIG. 11 shows the measured values of the effective diffusion length as a function of tumor mass for melanoma tumors.

Figure 12:
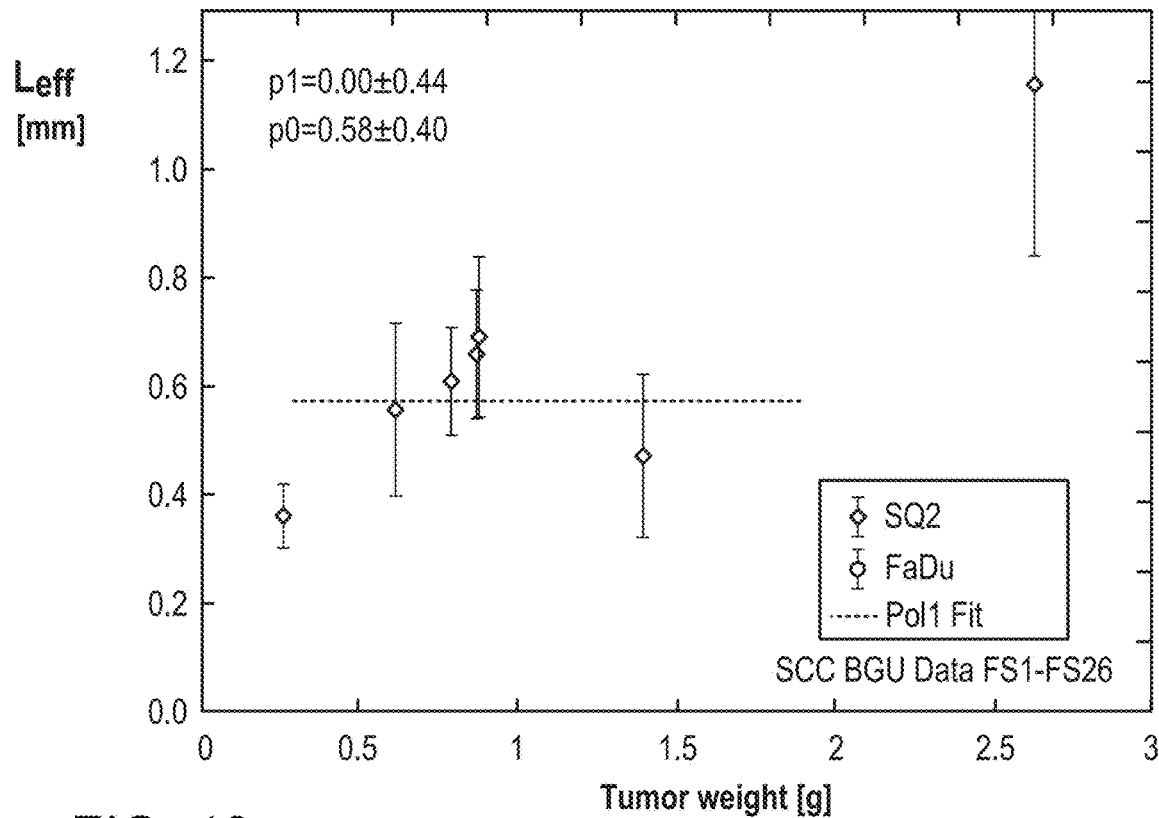

FIG. 12 shows the measured values of the effective diffusion length as a function of tumor mass for squamous cell carcinoma tumors.

Figure 13:
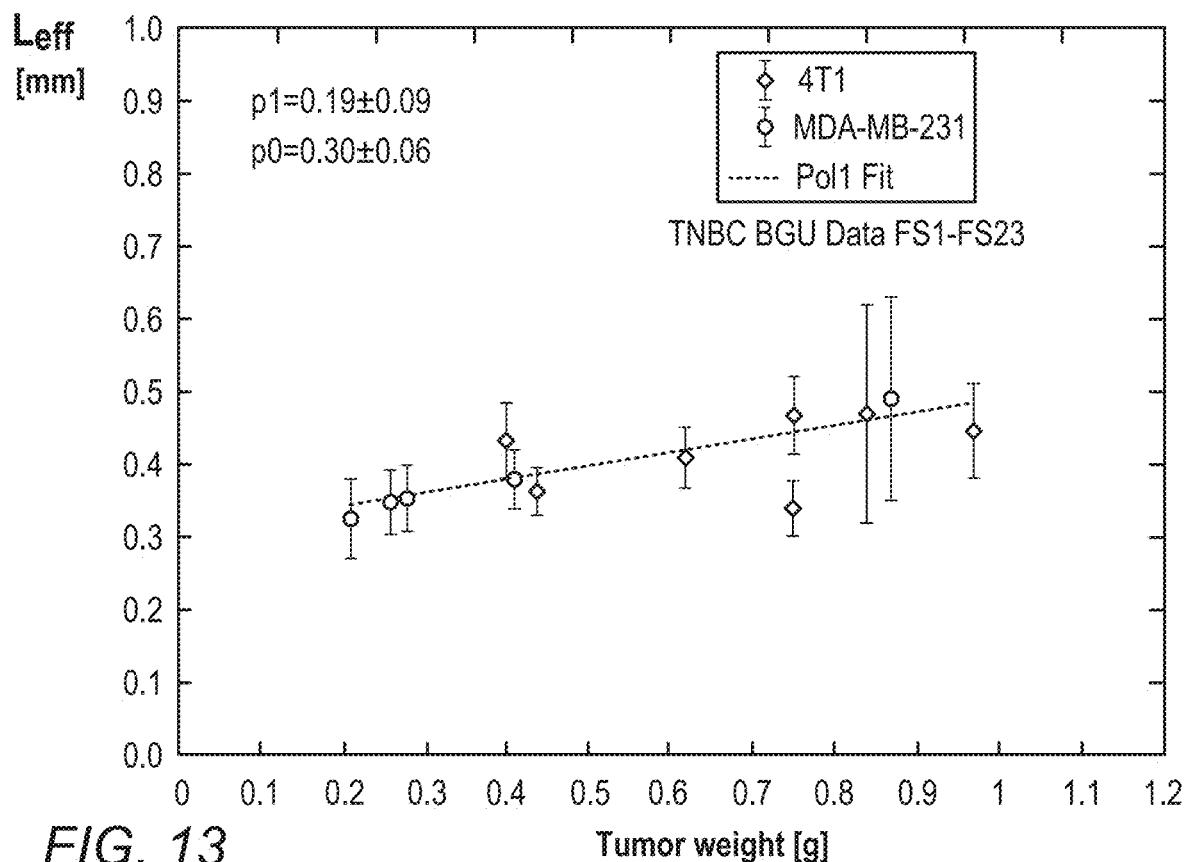

FIG. 13 shows the measured values of the effective diffusion length as a function of tumor mass for triple negative breast tumors.

Figure 14:
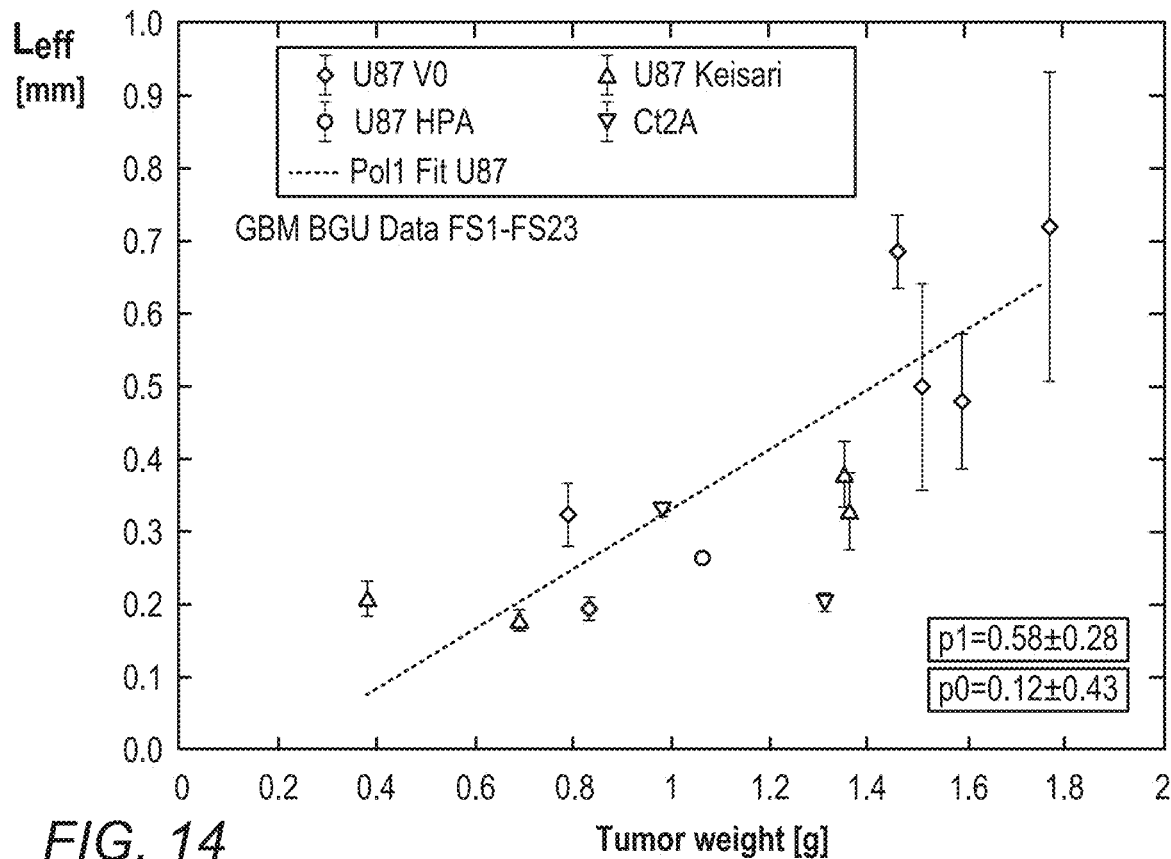

FIG. 14 shows the measured values of the effective diffusion length as a function of tumor mass for GBM tumors.

APPENDIX B

Rn Measurement Methodology

A DaRT seed is inserted to a tumor for a relatively short time—30 minutes, after which the seed is removed (in order to prevent the Pb buildup inside the tumor). The tumor is then set to freeze and cut into 10 μm-thick sections perpendicular to the seed axis. These are placed on glass slides and are fixed using Formaldehyde. The tumor sections are then taken to a digital autoradiography system (iQID alpha camera, by QScint Imaging Solutions, LLC), which records alpha particle hits one-by-one, providing their xy coordinates (with an accuracy of ~20 μm), a timestamp and a signal proportional to the deposited energy.

Figure 15:
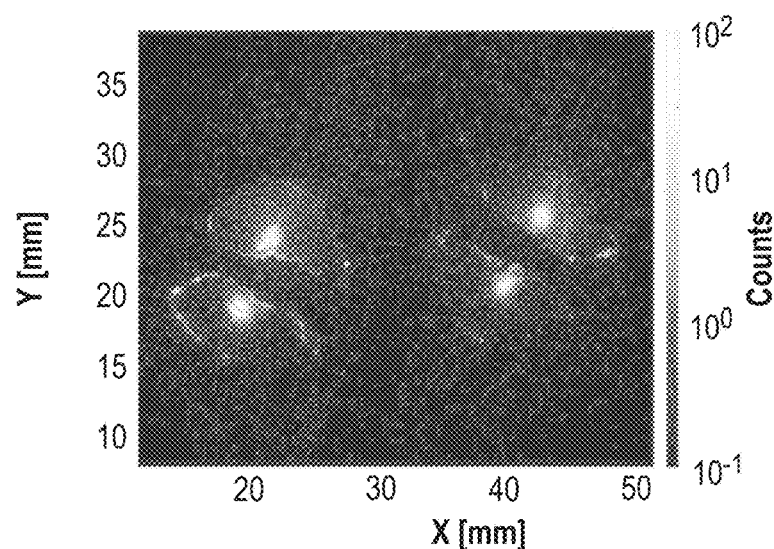
FIG. 15 shows Four histological sections of a DaRT treated tumor, acquired using a digital autoradiography system, for measurement of the radon-220 diffusion length.
Figure 16A:
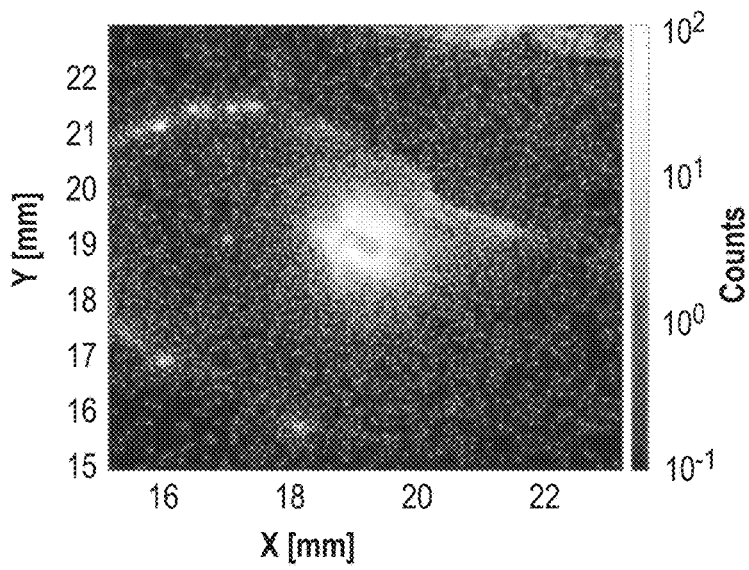
FIG. 16A shows a single histological section used for measurement of the radon-220 diffusion length.

An example for an image, consisting of four histological sections of a DaRT treated tumor and acquired using the iQID system is shown in FIG. 15, which shows four histological sections of a DaRT treated tumor, acquired using the iQID autoradiography system. For the analysis, the image is cropped so that each section is analyzed independently, as can be seen in FIG. 16A, which shows a single histological section used for the analysis. For each section, the center is chosen (either by a center-of-gravity method, or by identifying a "hole" in the activity map), and the average number of alpha particle counts is calculated at increased radial distances from the center. The resulting plot is then fitted numerically, by assuming that the recorded activity map is a superposition of infinitesimal segments along the DaRT seed, where each segment is calculated using eq. 1:

$$\Gamma(r) = \frac{A}{r} \cdot e^{\left(-\frac{L_{Rn}}{r}\right)} \qquad (1)$$

In this expression, r is the radial distance between the seed segment and the point-of-interest on the image, $L_{Rn}$ is the radon diffusion length and A is a free parameter. These two parameters ($L_{Rn}$, A) are found by a least-squares-fit approach.

Figure 16B:
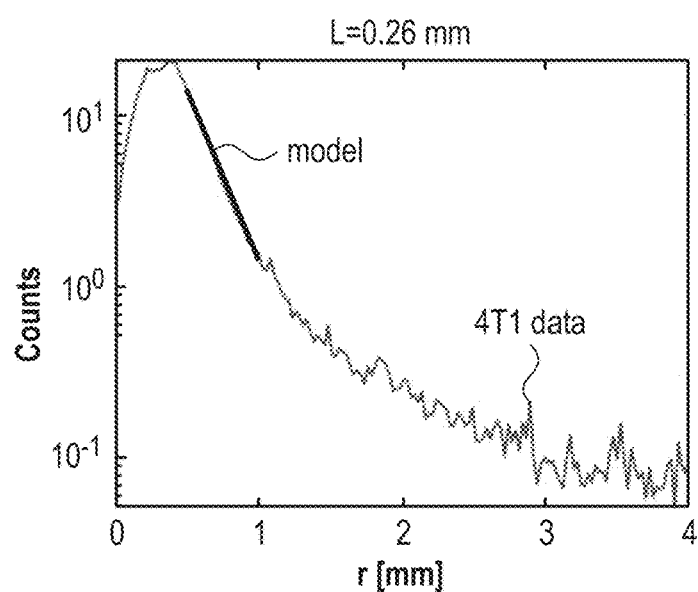
FIG. 16B shows calculated average counts as a function of distance from a seed location, with a fitted model used for measurement of the radon-220 diffusion length.

The fit is performed over a limited region of the activity distribution, to avoid the artificial "hole" in the center (where the DaRT seed was) and the far end of the distribution, where the statistical variation are too large. An example of a fitted curve is shown in FIG. 16B, which shows the calculated average counts as a function of distance from the seed location, including the fitted function.

The invention claimed is:

1. A method for treating a melanoma tumor, comprising:
   identifying a tumor as a melanoma tumor; and
   implanting in the tumor identified as a melanoma tumor, at least one diffusing alpha-emitter radiation therapy (DaRT) source with a suitable radon release rate and for a given duration, such that the at least one DaRT source provides during the given duration a cumulated activity of released radon between 3.2 Mega becquerel (MBq) hour and 7.5 MBq hour, per centimeter length,
   wherein implanting the at least one DaRT source comprises implanting an array of DaRT sources, each DaRT source separated from its neighboring DaRT sources in the array by between 3.1 and 3.9 millimeters.

2. The method of claim 1, wherein implanting the at least one DaRT source comprises implanting an array of DaRT sources in a hexagonal arrangement.

3. The method of claim 1, wherein the at least one DaRT source has a radon release rate of between 0.67 and 1.6 microcurie per centimeter length.

4. The method of claim 3, wherein the at least one DaRT source has a radon release rate of between 0.8 and 1.5 microcurie per centimeter length.

5. The method of claim 1, wherein the method comprises selecting the given duration before implanting the at least one DaRT source in the tumor, and removing the at least one DaRT source from the tumor after the given duration from the implanting of the at least one DaRT source has passed.

6. The method of claim 1, wherein the at least one DaRT source has a radon release rate of between 0.67 and 1.1 microcurie per centimeter length.

7. The method of claim 1, wherein the at least one DaRT source has a radon release rate of between 1.25 and 1.6 microcurie per centimeter length.

* * * * *